(12) United States Patent
Yoo et al.

(10) Patent No.: US 12,268,797 B2
(45) Date of Patent: *Apr. 8, 2025

(54) NON-CULTURED, PARTIALLY DIGESTED, CRYOPRESERVED CARTILAGE PRODUCT

(71) Applicant: OSIRIS THERAPEUTICS, INC., Columbia, MD (US)

(72) Inventors: Dana Sue Yoo, Falls Church, VA (US); Jin-Qiang Kuang, Woodstock, VA (US); Jaime Paden, Columbia, MD (US); Scott A. Maxson, Columbia, MD (US); Alla Danilkovitch, Columbia, MD (US); Erasmo Lopez, Somerville, NJ (US); Samson Tom, Basking Ridge, NJ (US)

(73) Assignee: OSIRIS THERAPEUTICS, INC., Columbia, MD (US)

( * ) Notice: Subject to any disclaimer, the term of this patent is extended or adjusted under 35 U.S.C. 154(b) by 165 days.

This patent is subject to a terminal disclaimer.

(21) Appl. No.: 17/681,064

(22) Filed: Feb. 25, 2022

(65) Prior Publication Data

US 2022/0184277 A1  Jun. 16, 2022

Related U.S. Application Data

(63) Continuation of application No. 14/485,210, filed on Sep. 12, 2014, now Pat. No. 11,406,735, which is a
(Continued)

(51) Int. Cl.
*A61L 27/36* (2006.01)
*A61K 35/32* (2015.01)
(Continued)

(52) U.S. Cl.
CPC .......... *A61L 27/3612* (2013.01); *A61K 35/32* (2013.01); *A61K 38/014* (2013.01);
(Continued)

(58) Field of Classification Search
None
See application file for complete search history.

(56) References Cited

U.S. PATENT DOCUMENTS

| 5,131,850 A | 7/1992 | Brockbank |
| 5,270,300 A | 12/1993 | Hunziker |

(Continued)

FOREIGN PATENT DOCUMENTS

| AU | 2013290064 | 7/2013 |
| AU | 2013290065 | 7/2013 |

(Continued)

OTHER PUBLICATIONS

U.S. Appl. No. 61/670,424, filed Jul. 11, 2012, Yoo, et al.
(Continued)

*Primary Examiner* — Isis A Ghali
(74) *Attorney, Agent, or Firm* — Norton Rose Fulbright US LLP

(57) ABSTRACT

This invention provides porated cartilage products and methods of producing porated cartilage products. Optionally, the cartilage products are sized, porated, and digested to provide a flexible cartilage product. Optionally, the cartilage products comprise viable chondrocytes, bioactive factors such as chondrogenic factors, and a collagen type II matrix. Optionally, the cartilage products are non-immunogenic.

26 Claims, 16 Drawing Sheets

Related U.S. Application Data continuation of application No. 13/939,991, filed on Jul. 11, 2013, now abandoned.

(60) Provisional application No. 61/670,434, filed on Jul. 11, 2012, provisional application No. 61/670,444, filed on Jul. 11, 2012, provisional application No. 61/670,424, filed on Jul. 11, 2012.

(51) Int. Cl.
| A61K 38/01 | (2006.01) |
|---|---|
| A61L 27/24 | (2006.01) |
| A61L 27/38 | (2006.01) |
| A61L 27/50 | (2006.01) |
| A61L 27/54 | (2006.01) |
| A61L 27/56 | (2006.01) |

(52) U.S. Cl.
CPC ........... *A61L 27/24* (2013.01); *A61L 27/3608* (2013.01); *A61L 27/3654* (2013.01); *A61L 27/3683* (2013.01); *A61L 27/3687* (2013.01); *A61L 27/3691* (2013.01); *A61L 27/3817* (2013.01); *A61L 27/3852* (2013.01); *A61L 27/50* (2013.01); *A61L 27/54* (2013.01); *A61L 27/56* (2013.01); *A61L 2300/414* (2013.01); *A61L 2300/64* (2013.01); *A61L 2430/06* (2013.01)

(56) References Cited

U.S. PATENT DOCUMENTS

| 5,326,357 | A |  | 7/1994 | Kandel |  |
|---|---|---|---|---|---|
| 5,853,746 | A |  | 12/1998 | Hunziker |  |
| 6,049,025 | A |  | 4/2000 | Stone et al. |  |
| 6,080,194 | A |  | 6/2000 | Pachence et al. |  |
| 6,132,468 | A | * | 10/2000 | Mansmann | A61F 2/38 |
|  |  |  |  |  | 623/18.11 |
| 6,235,316 | B1 |  | 5/2001 | Adkisson |  |
| 6,326,029 | B1 |  | 12/2001 | Geistlich et al. |  |
| 6,514,514 | B1 |  | 2/2003 | Atkinson et al. |  |
| 6,530,956 | B1 |  | 3/2003 | Mansmann |  |
| 6,645,764 | B1 |  | 11/2003 | Adkisson |  |
| 6,676,969 | B2 |  | 1/2004 | Geistlich et al. |  |
| 6,773,713 | B2 |  | 8/2004 | Bonassar et al. |  |
| 7,087,227 | B2 |  | 8/2006 | Adkisson |  |
| 7,157,222 | B2 |  | 1/2007 | Khirabadi et al. |  |
| 7,208,177 | B2 |  | 4/2007 | Geistlich et al. |  |
| 7,594,934 | B2 |  | 9/2009 | Stone |  |
| RE41,286 | E |  | 4/2010 | Atkinson et al. |  |
| 7,824,711 | B2 |  | 11/2010 | Kizer et al. |  |
| 8,173,162 | B2 |  | 5/2012 | Vilei et al. |  |
| 8,193,317 | B2 |  | 6/2012 | Yayon et al. |  |
| 10,874,763 | B2 |  | 12/2020 | Yoo et al. |  |
| 2001/0016772 | A1 |  | 8/2001 | Lee et al. |  |
| 2002/0013627 | A1 |  | 1/2002 | Geistlich et al. |  |
| 2002/0048595 | A1 |  | 4/2002 | Geistlich et al. |  |
| 2002/0173806 | A1 |  | 11/2002 | Giannetti et al. |  |
| 2003/0077821 | A1 |  | 4/2003 | Sah et al. |  |
| 2003/0095994 | A1 |  | 5/2003 | Geistlich et al. |  |
| 2004/0213852 | A1 |  | 10/2004 | Van Kuppevelt et al. |  |
| 2004/0230303 | A1 |  | 11/2004 | Gomes et al. |  |
| 2006/0275273 | A1 |  | 12/2006 | Seyedin et al. |  |
| 2007/0038299 | A1 |  | 2/2007 | Stone et al. |  |
| 2007/0065943 | A1 |  | 3/2007 | Smith et al. |  |
| 2007/0077237 | A1 |  | 4/2007 | Damari et al. |  |
| 2007/0128174 | A1 |  | 6/2007 | Kleinsek et al. |  |
| 2007/0154563 | A1 |  | 7/2007 | Behnam et al. |  |
| 2007/0178074 | A1 | * | 8/2007 | Hu | C12N 5/0655 |
|  |  |  |  |  | 435/325 |
| 2007/0250164 | A1 |  | 10/2007 | Troxel |  |
| 2007/0299517 | A1 |  | 12/2007 | Davisson et al. |  |
| 2008/0160496 | A1 |  | 7/2008 | Rzepakovskv et al. |  |
| 2008/0269895 | A1 |  | 10/2008 | Steinwachs et al. |  |
| 2009/0024223 | A1 |  | 1/2009 | Chen et al. |  |
| 2009/0024224 | A1 |  | 1/2009 | Chen et al. |  |
| 2009/0024229 | A1 |  | 1/2009 | Chen et al. |  |
| 2009/0291112 | A1 |  | 11/2009 | Truncale et al. |  |
| 2010/0010638 | A1 |  | 1/2010 | Jones et al. |  |
| 2010/0274362 | A1 |  | 10/2010 | Yayon et al. |  |
| 2011/0238180 | A1 |  | 9/2011 | Fritz et al. |  |
| 2011/0262554 | A1 |  | 10/2011 | Masinaei et al. |  |
| 2012/0009224 | A1 |  | 1/2012 | Kizer et al. |  |
| 2012/0009270 | A1 |  | 1/2012 | Kizer et al. |  |
| 2012/0039961 | A1 |  | 2/2012 | Mollenhauer |  |
| 2012/0087948 | A1 |  | 4/2012 | Kizer et al. |  |
| 2014/0017283 | A1 |  | 1/2014 | Yoo et al. |  |
| 2014/0017292 | A1 |  | 1/2014 | Yoo et al. |  |
| 2014/0030309 | A1 |  | 1/2014 | Yoo et al. |  |
| 2015/0004211 | A1 |  | 1/2015 | Yoo et al. |  |
| 2015/0017222 | A1 |  | 1/2015 | Yoo et al. |  |
| 2015/0140057 | A1 |  | 5/2015 | Yoo et al. |  |

FOREIGN PATENT DOCUMENTS

| AU | 2013290152 | 7/2013 |
|---|---|---|
| BR | 112015000668.0 | 7/2013 |
| BR | 112015000669.8 | 7/2013 |
| BR | 112015000670.1 | 7/2013 |
| CA | 2878802 | 7/2013 |
| CA | 2878808 | 7/2013 |
| CA | 2878921 | 7/2013 |
| CN | 102526806 | 7/2012 |
| EP | 1254670 | 11/2002 |
| EP | 1738717 | 1/2007 |
| EP | 1784117 | 1/2008 |
| EP | 13816519.6 | 7/2013 |
| EP | 13817485.9 | 7/2013 |
| EP | 13817610.2 | 7/2013 |
| JP | 2002505144 | 2/2002 |
| JP | 2009508596 | 3/2009 |
| JP | 2009508600 | 3/2009 |
| KR | 10-2015-7003679 | 7/2013 |
| KR | 10-2015-7003680 | 7/2013 |
| KR | 10-2015-7003681 | 7/2013 |
| MX | MX/a/2015/000458 | 7/2013 |
| MX | MX/a/2015/000460 | 7/2013 |
| MX | MX/a/2015/000463 | 7/2013 |
| SG | 11201500181 | 7/2013 |
| SG | 11201500187 W | 7/2013 |
| SG | 11201500189 | 7/2013 |
| WO | WO 1996/025961 | 8/1996 |
| WO | WO 1999/019005 | 4/1999 |
| WO | WO 1999/044533 | 9/1999 |
| WO | WO 2000/015153 | 3/2000 |
| WO | WO 2001/006949 | 2/2001 |
| WO | WO 2003/028545 | 4/2003 |
| WO | WO 2003/092542 | 11/2003 |
| WO | WO 2003/094703 | 11/2003 |
| WO | WO 2009/005596 | 1/2009 |
| WO | WO 2009/125402 | 10/2009 |
| WO | WO 2011/105724 | 9/2011 |
| WO | WO 2014/011889 | 7/2013 |
| WO | WO 2014/011890 | 7/2013 |
| WO | WO 2014/011891 | 7/2013 |

OTHER PUBLICATIONS

U.S. Appl. No. 61/670,434, filed Jul. 11, 2012, Yoo, et al.
U.S. Appl. No. 61/670,444, filed Jul. 11, 2012, Yoo, et al.
"Hyaline Cartilage," as accessed from the Internet on Jun. 22, 2017 from https://en.wikipedia.oro/wiki/Hyaline_cartilage (3 pages).
Advisory Action issued on Sep. 28, 2017 by the U.S. Patent and Trademark Office for U.S. Appl. No. 14/498,394, filed Sep. 26, 2014 and published as US 2015/0017222 on Jan. 15, 2015(Inventor—Yoo et al..; Applicant—Osiris Therapeutics, Inc.) (17 pages).
Alford, J.W., M.D. and B.J. Cole, M.D., M.B.A., Cartilage Restoration, Part 1: Basic Science, Historical Perspective, Patient Evaluation, and Treatment Options, Am J Sports Med, 33(2): 295-306 (2005).
Amendment and Response to Final Office Action filed on Jul. 4, 2016 by the U.S. Patent and Trademark Office for U.S. Appl. No.

(56) References Cited

OTHER PUBLICATIONS

14/498,394, filed Sep. 26, 2014 and published as US 2015/0017222 on Jan. 15, 2015 (Inventor—Yoo et al..; Applicant—Osiris Therapeutics, Inc.) (13 pages).
Bardos, et al.. "Osteochondral integration of multiply incised pure cartilage allograft: repair method of focal chondral defects in a porcine model," Am. J. Sports Med., 37: 50S (2009).
Bos, et al.. "Specific enzymatic treatment of bovine and human articular cartilage," *Arthritis & Rheumatism*, vol. 46, No. 4, pp. 976-985 (2002).
Bravenboer, et al.. "Improved cartilage integration and interfacial strength after enzymatic treatment in a cartilage transplantation model," *Arthritis Res. Ther.*, vol. 6 (2004).
Certificate of Grant issued on Feb. 16, 2017 by the Australian Patent Office for Patent Application No. 2013290152, which was filed on Jul. 11, 2013 and granted as AU 2013290152 on Feb. 16, 2017 (Applicant—Osiris Therapeutics, Inc.) (1 page).
Cheng et al.., "Chondrogenic differentiation of adipose-derived adult stem cells by a porous scaffold derived from native articular cartilage extracellular matrix," *Tissue Engineering: Part A*, 2009, vol. 15, pp. 231-241.
Clar et al.., "Clinical and cost-effectiveness of autologous chondrocyte implantation for cartilage defects in knee joints: systematic review and economic evaluation," *Health Technology Assessment* 2005, vol. 9: No. 47, 1-82.
Csonge, L., et al.., "Banking of osteochondral allografts, Part II. Preservation of Condrocyte Viability During Long-Term Storage," *Cell and Tissue Banking* 3: 161-168 (2002).
Curran et al.., "The uptake of labelled sulphate by human cartilage cells and its use as a test for viability," *Proc R Soc Lond B Biol Sci.* 1955, 144(917):572-6.
Elder et al.., "Extraction techniques for the decellularization of tissue engineered articular cartilage constructs," *Biomaterials* 2009, vol. 30, pp. 3749-3756.
European Search Report issued on Feb. 12, 2016 for application EP 13817610, filed on Jul. 11, 2014 and published as EP 2874571 on May 27, 2015 (Applicant—Osiris Therapeutics, Inc.// Inventor—Yoo, et al..) (6 pages).
European Search Report issued on Feb. 12, 2016 for application EP 13817485, filed on Jul. 11, 2013 and published as EP 2872189 on May 20, 2015 (Applicant—Osiris Therapeutics, Inc.//Inventor—Yoo, et al..) (6 pages).
European Search Report issued on Mar. 22, 2016 for application EP 13816519.6, filed on Feb. 5, 2015 and published as EP 2872071 on May 20, 2015 (Applicant—Osiris Therapeutics, Inc.// Inventor—Yoo, et al..) (6 pages).
Examination Report No. 1 issued on Feb. 16, 2017 by the Commonwealth of Australia Patents Office for Patent Application No. 2013290065, which was filed on Jul. 11, 2013 (Inventor—Yoo et al.; Applicant—Osiris Therapeutics, Inc.) (4 pages).
Examination Report No. 1 issued on Jul. 3, 2017 by the Commonwealth of Australian Patent Office for Patent Application No. 2013290064, which was filed on Jul. 11, 2013 (Inventor—Yoo et al..; Applicant—Osiris Therapeutics, Inc.) (3 pages).
Final Office Action issued on May 10, 2017 by the U.S. Patent and Trademark Office for U.S. Appl. No. 14/498,394, filed Sep. 26, 2014 and published as US 2015/0017222 on Jan. 15, 2015(Inventor—Yoo et al.; Applicant—Osiris Therapeutics, Inc.) (20 pages).
Final Office Action issued on Dec. 1, 2016 the U.S. Patent and Trademark Office for U.S. Appl. No. 14/464,123, filed Aug. 20, 2014 and published as US-2015-0140057-A1 on May 21, 2015 (Inventor—Yoo, et al.. II Applicant—Osiris Therapeutics. Inc.) (23 pages).
Final Office Action issued on Nov. 16, 2018 by the U.S. Patent and Trademark Office for U.S. Appl. No. 14/498,394, filed Sep. 26, 2014 and published as US 2015/0017222 on Jan. 15, 2015 (Inventor—Yoo et al..; Applicant—Osiris Therapeutics, Inc.) (25 pages).
Final Office Action issued on Sep. 1, 2015 by the U.S. Patent and Trademark Office for U.S. Appl. No. 14/498,394, filed Sep. 26, 2014 and published as US 2015/0017222 on Jan. 15, 2015 (Inventor—Yoo et al..; Applicant—Osiris Therapeutics, Inc.;) (25 pages).
Final Rejection issued on Jan. 2, 2018 by the U.S. Patent and Trademark Office for U.S. Appl. No. 14/464,123, filed Aug. 20, 2014 and published as US 2015/0140057 A1 on May 21, 2015 (Inventor—Dana Sue Yoo) (24 pages).
Final Rejection was mailed on Jul. 16, 2019 by the USPTO for U.S. Appl. No. 14/464,123, filed Aug. 20, 2014 and published as US 2015/0140057 A 1 on May 21, 2015 (Inventor—Dana Sue Yoo) (22 Pages).
Fortier, L., et al.. , "The Role of Growth Factors in Cartilage Repair," *Clin Orthop Relat Res* 469: pp. 2706-2715 (Mar. 15, 2011).
Fox, A.J.S et al.., "The Basic Science of Articular Cartilage: Structure, Composition, and Function," *Sports Health* 2009; 1 (6):461-8.
Goldring, Mary B. "Chondrogenesis, chondrocyte differentiation, and articular cartilage metabolism in health and osteoarthritis," *Ther Adv Musculoskel Dis* 2012, 4(4), 269-285.
Gole, M.D. et al.., "Chondrocyte Viability in Press-Fit Cryopreserved Osteochondral Allografts," *J Orthopedic Res*, 22(4): 781-7 (2004).
International Preliminary Report on Patentability issued Jan. 13, 2015 for International Patent Application No. PCT/US2013/050089, filed on Jul. 11, 2013 and published as WO 2014/011889 on Jan. 16, 2014 (Inventor—Yoo; Applicant—Osiris Therapeutics, Inc.)(pp. 1-1).
International Preliminary Report on Patentability issued Jan. 13, 2015 for International Patent Application No. PCT/US2013/050093, filed on Jul. 11, 2013 and published as WO 2014/011890 on Jan. 16, 2014 (Inventor—Yoo; Applicant—Osiris Therapeutics, Inc.)(pp. 1-1).
International Preliminary Report on Patentability issued Jan. 13, 2015 for International Patent Application No. PCT/US2013/050094, filed on Jul. 11, 2013 and published as WO 2014/011891 on Jan. 16, 2014 (Inventor—Yoo; Applicant—Osiris Therapeutics, Inc.)(pp. 1-1).
International Search Report and Written Opinion issued Nov. 22, 2013 for International Patent Application No. PCT/US2013/050089, filed on Jul. 11, 2013 and published as WO 2014/011889 on Jan. 16, 2014 (Inventor—Yoo; Applicant—Osiris Therapeutics, Inc.)(pp. 1-8).
International Search Report and Written Opinion issued Sep. 17, 2013 for International Patent Application No. PCT/US2013/050093, filed on Jul. 11, 2013 and published as WO 2014/011890 on Jan. 16, 2014 (Inventor—Yoo; Applicant—Osiris Therapeutics, Inc.)(pp. 1-7).
International Search Report and Written Opinion issued Sep. 20, 2013 for International Patent Application No. PCT/US2013/050094, filed on Jul. 11, 2013 and published as WO 2014/011891 on Jan. 16, 2014 (Inventor—Yoo; Applicant—Osiris Therapeutics, Inc.)(pp. 1-9).
Kulyk et al.. "Strategic Design and Fabrication of Engineered Scaffolds for Articular Cartilage Repair," *J. Funct. Biomater* 2012, 3, 799-838.
Lotz, et al.. "The chemical structure and the crystalline structures of bombyx mori silk fibroin," *Biochimie*, vol. 61 :2, pp. 205-214 (1979).
Non Final Rejection issued on Mar. 24, 2017 by the U.S. Patent and Trademark Office for U.S. Appl. No. 14/464,123, filed Aug. 20, 2014 and published as US 2015/0140057 A1 on May 21, 2015 (Inventor—Dana Sue Yoo) (23 pages).
Non Final Rejection was mailed on Jun. 25, 2019 by the US PTO for U.S. Appl. No. 14/498,394, filed Sep. 26, 2014 and published as US 2015/0017222 A 1 on Jan. 15, 2015 (Inventor—Dana Sue Yoo) (17 Pages).
Non-Final Office Action issued Jan. 28, 15 for U.S. Appl. No. 14/498,394, filed Sep. 26, 14 and published as U.S. 2015/0017222 on Jan. 15, 2015 (Inventor—Yoo; Applicant—Osiris Therapeutics, Inc.)(pp. 1-18).
Non-Final Office Action issued on Apr. 27, 2018 by the U.S. Patent and Trademark Office for U.S. Appl. No. 14/498,394, filed Sep. 26, 2014 and published as US 2015/0017222 on Jan. 15, 2015 (Inventor—Yoo et al..; Applicant—Osiris Therapeutics, Inc.) (20 pages).

(56) References Cited

OTHER PUBLICATIONS

Non-Final Office Action issued on Apr. 15, 2016 the U.S. Patent and Trademark Office for U.S. Appl. No. 14/464,123, filed Aug. 20, 2014 and published as US-2015-0140057-A 1 on May 21, 2015 (Inventor—Yoo, et al.. II Applicant—Osiris Therapeutics. Inc.) (23 pages).
Non-Final Office Action issued on Mar. 31, 2016 by the U.S. Patent and Trademark Office for U.S. Appl. No. 14/498,394, filed Sep. 26, 2014 and published as US 2015/0017222 on Jan. 15, 2015 (Inventor—Yoo et al..; Applicant—Osiris Therapeutics, Inc.) (19 pages).
Non-Final Office Action issued on Oct. 17, 2016 by the U.S. Patent and Trademark Office for U.S. Appl. No. 14/498,394, filed Sep. 26, 2014 and published as US 2015/0017222 on Jan. 15, 2015 (Inventor—Yoo et al..; Applican—Osiris Therapeutics, Inc.) (17 pages).
Office Action issued in corresponding Canadian Application No. 2,878,808, dated Jan. 30, 2020.
Office Action issued on Apr. 4, 2017 by the Japan Patent Office for Japanese Patent Application No. 2015-521811, which was filed on Jul. 11, 2013 (Inventor—Yoo et al..; Applicant—Osiris Therapeutics, Inc.) (Original—4 pages/ Translation: 5 pages).
Office Action issued on Jun. 6, 2017 by the Japan Patent Office for Japanese Patent Application No. 2015-521812, which was filed on Jul. 22, 2013 (Inventor—Yoo et al..; Applicant—Osiris Therapeutics, Inc.) (Original—6 pages/ Translation—9 pages).
Office Action issued on Jun. 22, 2017 by the Mexican Institute of Intellectual Property for Mexican Patent Application No. MX/A/2015/000460, which was filed on Jul. 11, 2013 and published on Aug. 14, 2015 (Inventor—Yoo et al..; Applicant—Osiris Therapeutics, Inc.) (Original—4 pages/ Translation—4 pages).
Office Action issued on Jun. 28, 2017 by the Mexican Institute of Intellectual Property for Mexican Patent Application No. MX/A/2015/000463, which was filed on Jul. 11, 2013 and published as Sep. 9, 2015 (Inventor—Yoo et al..; Applicant—Osiris Therapeutics, Inc.) (Original—5 pages/ Translation—5 pages).
Office Action issued on Jul. 4, 2017 by the Japan Patent Office for Japanese Patent Application No. 2015-521813, which was filed on Jul. 11, 2013 (Inventor—Yoo et al.; Applicant—Osiris Therapeutics, Inc.) (Original—4 pages/ Translation—4 pages).
Office Action issued on May 2, 2019 by the Canadian Intellectual Property Office for Patent Application No. 2,878,921, which was filed on Jul. 11, 2013 (Applicant—Osiris Therapeutics, Inc.) (3 pages).
Office Action issued on Aug. 29, 2018 by the Canadian Intellectual Property Office for Patent Application No. 2878808, which was filed on Jan. 8, 2015 (Inventor—Yoo et al..; Applicant—Osiris Therapeutics, Inc.) (4 pages).
Office Action issued on Jul. 27, 2018 by the Canadian Intellectual Property Office for Patent Application No. 2,878,921, which was filed on Jan. 9, 2015 (Inventor—Yoo et al..; Applicant—Osiris Therapeutics, Inc.) (3 pages).
Office Action issued on Jun. 18, 2018 by the Canadian Intellectual Property Office for Patent Application No. 2,878,802, which was filed on Jan. 8, 2015 (Inventor—Yoo et al..; Applicant—Osiris Therapeutics, Inc.) (4 pages).
Office Action was mailed on Jun. 6, 2019 by the Canadian Patent Office for CA Application No. 2878808, filed on Jul. 11, 2013 and published as CA 2878808 A 1 on Jan. 16, 2014 (Applicant—Osiris Therapeutics, Inc.) (3 Pages).
Preliminary Amendment filed Sep. 26, 2014 for U.S. Appl. No. 14/498,394, filed Sep. 26, 2014 and published as U.S. 2015/0017222 on Jan. 15, 2015 (Inventor—Yoo; Applicant—Osiris Therapeutics, Inc.)(pp. 1-3).
Preliminary Amendment filed on Jul. 15, 2015 with the U.S. Patent and Trademark Office for U.S. Appl. No. 14/464,123, filed Aug. 20, 2014 and published as US 2015/0140057 on May 21, 2015 (Inventor—Yoo et al..; Applicant—Osiris Therapeutics, Inc.) (6 pages).

Quinn, et al.., "Variation Of Cell And Matrix Morphologies In Articular Cartilage Among Locations In The Adult Human Knee," Osteoarthritis and Cartilage, Aug. 2005, vol. 13, No. 8, pp. 672-678.
Response to Final Rejection and Request for Continued Examination (RCE) mailed on Feb. 21, 2017 to the U.S. Patent and Trademark Office for U.S. Appl. No. 14/464,123, filed Aug. 20, 2014 and published as US 2015/0140057 A 1 on May 21, 2015 (Inventor—Dana Sue Yoo) (13 pages).
Response to Final Rejection and Request for Continued Examination (RCE) filed on Jul. 2, 2018 with the U.S. Patent and Trademark Office for U.S. Appl. No. 14/464,123, filed Aug. 20, 2014 and published as US 2015/0140057 A1 on May 21, 2015 (Inventor—Dana Sue Yoo) (19 pages).
Response to Final Rejection and Request for Continued Examination (RCE) filed on Nov. 10, 2017 with the U.S. Patent and Trademark Office for U.S. Appl. No. 14/498,394, filed Sep. 26, 2014 and published as US 2015/0017222 on Jan. 15, 2015(Inventor—Yoo et al..; Applicant—Osiris Therapeutics, Inc.) (15 pages).
Response to Non Final Rejection mailed on Sep. 22, 2017 to the U.S. Patent and Trademark Office for U.S. Appl. No. 14/464,123, filed Aug. 20, 2014 and published as US 2015/0140057 A1 on May 21, 2015 (Inventor—Dana Sue Yoo) (13 pages).
Response to Non-Final Office Action filed on Feb. 16, 2017 with the U.S. Patent and Trademark Office for U.S. Appl. No. 14/498,394, filed Sep. 26, 2014 and published as US 2015/0017222 on Jan. 15, 2015(Inventor—Yoo et al.; Applicant—Osiris Therapeutics, Inc.) (14 pages).
Response to Non-Final Office Action filed on May 28, 2015 with the U.S. Patent and Trademark Office for U.S. Appl. No. 14/498,394, filed Sep. 26, 2014 and published as US 2015/0017222 on Jan. 15, 2015 (Inventor—Yoo et al..; Applicant—Osiris Therapeutics, Inc.) (26 pages).
Rosett, T. "An improved Grinding apparatus for the disruption of fibrous tissue," *The Journal of Investigative Dermatology* 1963, 41, 357-359.
Search Report issued by the IP Office of Singapore on Mar. 1, 2016 for application 11201500189P, filed on Jul. 11, 2013 (Applicant—Osiris Therapeutics, Inc.) (4 pages).
Search Report issued by the IP Office of Singapore on Mar. 1, 2016 for application 11201500187W, filed on Jul. 11, 2013 (Applicant—Osiris Therapeutics, Inc.) (3 pages).
Search Report issued by the IP Office of Singapore on Mar. 8, 2016 for application 11201500181U, filed on Jul. 11, 2013 (Applicant—Osiris Therapeutics, Inc.) (3 pages).
Wang, et al.., "Creating a living hyaline cartilage graft free from non-cartilaginous constituents: an intermediate role of a biomaterial scaffold," *Advanced Functional Materials*, 2012, vol. 22, pp. 972-978.
Written Opinion issued by the IP Office of Singapore on Mar. 1, 2016 for application 11201500189P, filed on Jul. 11, 2013 (Applicant—Osiris Therapeutics, Inc.) (9 pages).
Written Opinion issued by the IP Office of Singapore on Mar. 1, 2016 for application 11201500187W, filed on Jul. 11, 2013 (Applicant—Osiris Therapeutics, Inc.) (8 pages).
Written Opinion issued by the IP Office of Singapore on Mar. 8, 2016 for application 11201500181U, filed on Jul. 11, 2013 (Applicant—Osiris Therapeutics, Inc.) (8 pages).
Written Opinion issued on Jun. 16, 2017 by the Intellectual Property Office of Singapore for Singaporean Patent Application No. 11201500189P, which was filed on Jul. 11, 2013 (Inventor—Yoo et al..; Applicant—Osiris Therapeutics, Inc.) (9 pages).
Yang, Q., et al.., "A cartilage ECM-derived 3-D porous acellular matrix scaffold for in vivo cartilage tissue engineering with PKH26-labeled chondrogenic bone marrow-derived mesenchymal stem cells," Biomaterials, 2008, vol. 29, pp. 2378-2387.
Yang, Z. et al.., "Fabrication and Repair of Cartilage Defects with a Novel Acellular Cartilage Matrix Scaffold," *Tissue Eng Pt C Methods*. 2010; 16(5):865-76.

\* cited by examiner

A

B

A

B

A

B

A

B

C

A

B

A

B

C

D

A

B

A

B

NON-CULTURED, PARTIALLY DIGESTED, CRYOPRESERVED CARTILAGE PRODUCT

CROSS REFERENCE TO RELATED APPLICATIONS

This application is a continuation of U.S. application Ser. No. 14/485,210, filed Sep. 12, 2014, which is a continuation of U.S. application Ser. No. 13/939,991, filed Jul. 11, 2013, which claims the benefit of U.S. Provisional Application 61/670,444, filed Jul. 11, 2012, U.S. Provisional Application 61/670,434, filed Jul. 11, 2012, and U.S. Provisional Application 61/670,424, filed Jul. 11, 2012. The contents of each of the referenced applications are incorporated into the present application by reference.

The contents of related applications U.S. application Ser. No. 13/939,981, filed Jul. 11, 2013, PCT Application PCT/US2013/050093, filed Jul. 11, 2013, U.S. application Ser. No. 13/939,969, filed Jul. 11, 2013, and PCT Application PCT/US2013/050089, filed Jul. 11, 2013, are also incorporated into the present application by reference.

TECHNICAL FIELD

The present invention relates to cartilage products useful in therapeutics and methods of producing and using such therapeutics.

BACKGROUND

Articular cartilage injury remains one of the major unsolved problems in orthopedics. Over 500,000 patients per year in the U.S. undergo surgical procedures to repair cartilage damage. However, many of these surgeries yield suboptimal results.

Articular cartilage consists primarily of a sparse population of chondrocytes distributed throughout an extracellular matrix formed by proteoglycans in a type II collagen fibril. The collagens give the tissue its form and tensile strength and the interaction of proteoglycans with water give the tissue its stiffness to compression, resilience and durability. The hyaline cartilage provides a low friction bearing surface over the bony parts of the joint. If the lining becomes worn or damaged resulting in lesions, joint movement may be painful or severely restricted. Whereas damaged bone typically can regenerate successfully, hyaline cartilage regeneration is quite limited.

Current surgical treatments include microfracture, debridement, osteochondral grafting, and autologous chondrocyte implantation (ACI). The goal of these treatments is to repair and regenerate native hyaline cartilage (collagen type II).

Microfracturing involves the removal of damaged articular cartilage followed by physically insulting the underlying subchondral bone to exposed bone marrow and create bleeding. Although the blood clot introduces inflammatory cytokines, growth factors and MSCs to fill the defect, the process fails to produce articular cartilage and instead stimulates the production of fibrocartilage scar tissue, made from collagen type I. Fibrocartilage has poor long-term biomechanical performance, causes abnormal bone growth, and increases risk of osteoarthritis.

Other strategies that have fallen short include autologous chondrocyte implantation (ACI), debridement, and osteochondral grafting.

Gomes et al. (US 2004/0230303) describes an implant having a subchondral bone base and an articular cartilage cap containing bores drilled through the cartilage cap and base to allow cell migration. The implant can be digested with hyaluronidase (type IV-s, 3 mg/mL) and trypsin (0.25% in monodibasic buffer 3 ml) for 18 hours at 37° C. Among other shortcomings, Gomes et al. do not teach a flexible cartilage implant, a cartilage implant containing viable native chondrocytes, or a non-immunogenic cartilage implant.

Chen et al. (US 2009/0024229) describes a cartilage graft that is devitalized (made acellular) and then recellularized. The graft can be microperforated to facilitate recellularization. The graft can be devitalized using enzymes to modify the molecular aspects of the cartilage such as chondroitinase to remove proteoglycan and a recombinant endonuclease, for example BENZONASE® (Merk, Inc.). Among other shortcomings, Chen et al. do not teach a flexible cartilage implant or a cartilage implant containing viable native chondrocytes or a non-immunogenic cartilage implant.

Steinwachs et al. (US 2008/0269895) describes cartilage implants having various features. The implant can be a grown in-vitro from chondrocytes or can be a cartilage explant. Among various features, the implant can have channels with a diameter of 0.5 mm to 2 mm. Among other shortcomings, Steinwachs et al. do not teach a digested cartilage implant or a non-immunogenic cartilage implant.

Bardos et al. ("Osteochondral Integration of Multiply Incised Pure Cartilage Allograft: Repair Method of Focal Chondral Defects in a Porcine Model"; Am J Sports Med 2009 37: 50S) describes a pig cartilage sample comprising parallel incisions. Among other shortcomings, Bardos et al. do not teach a digested cartilage sample or a non-immunogenic cartilage sample.

Bravenboer et al. ("Improved cartilage integration and interfacial strength after enzymatic treatment in a cartilage transplantation model"; Arthritis Res Ther 2004, 6) describes bovine articular cartilage treated with hyaluronidase followed by collagenase. Among other shortcomings, Bravenboer et al. do not teach a cartilage sample comprising a plurality of pores or a non-immunogenic cartilage sample.

Bos et al. ("Specific Enzymatic Treatment of Bovine and Human Articular Cartilage"; Arthritis & Rheumatism Vol. 46, No. 4, April 2002, pp 976-985) describes cartilage samples treated with collagenase VII. Among other shortcomings, Bos et al. do not teach a cartilage sample comprising a plurality of pores or a non-immunogenic cartilage sample.

What is needed in the art is a flexible cartilage product that can be easily administered, for example, through an arthroscope cannula, and contoured to a site of injured cartilage and provides a collagen type II matrix containing viable chondrocytes and chondrogenic factors for regeneration of cartilage with minimal scarring.

SUMMARY OF THE INVENTION

The invention provides a method of making a cartilage product comprising providing a cartilage sample, porating the cartilage sample; and partially digesting the cartilage sample.

Exemplary methods of manufacture of the present invention have one or more (e.g. each) of the following technical features:
  partial digestion is performed in a manner that retains a substantial amount of viable cells;
  the cartilage sample is porated to an extent that increases flexibility of the cartilage sample;
  the cartilage sample comprises hyaline cartilage; and the cartilage sample is cryopreserved, e.g. after the steps of poration and partial digestion.

In one embodiment, the step of partial digestion is performed in a manner that retains a substantial amount of viable cells, for example, by limiting digestion to a cell-sparing amount. Optionally, said step of partial digestion comprises digesting collagen. Optionally, said step of partial digestion comprises enzyme digestion, e.g. digestion with a proteinase such as collagenase (e.g. collagenase Type II).

In one embodiment, the cartilage sample is porated to an extent that increases flexibility of the cartilage sample. Optionally, the cartilage sample is porated to provide pores having a diameter of about 0.2 mm to about 1.5 mm (e.g. about 1 mm) in diameter. Optionally, the cartilage sample is porated to provide about 10 to about 500 pores per $cm^2$, such as about 10 to about 60 pores per $cm^2$. Optionally, the cartilage sample comprises one or more layers of cartilage and the pores pass through the majority (e.g. entirety) of the one or more layers of cartilage.

In one embodiment, the cartilage sample comprises hyaline cartilage. Optionally, the cartilage sample is an articular cartilage sample. Optionally, the cartilage sample is isolated from subchondral bone and/or calcified cartilage.

In one embodiment, the cartilage sample is cryopreserved after the steps of poration and partial digestion. Optionally, the step of cryopreservation comprises cryopreserving in a manner that spares viable cells.

In some embodiments, the cartilage products of the present invention are not digested. In other embodiments, the cartilage products of the present invention are partially digested by digestive means including enzymatic (e.g. collegenase, pronase, proteinase K, etc. treatment), biochemical (e.g. papain), thermal (e.g. increased heat), chemical (keratin sulfate, tosyllysylchloromethane), mechanical (perforated), any other means of digestion known by those of skill in the art, and combinations of any two or more of the foregoing.

BRIEF DESCRIPTION OF THE DRAWINGS

FIG. 15A depicts the names used herein to reference surfaces of the cartilage product. FIG. 15B illustrates the diameter used for surface area calculation, the height used for thickness calculation, and the optional orientation of layers or gradient.

DETAILED DESCRIPTION OF THE INVENTION

Figure 1:
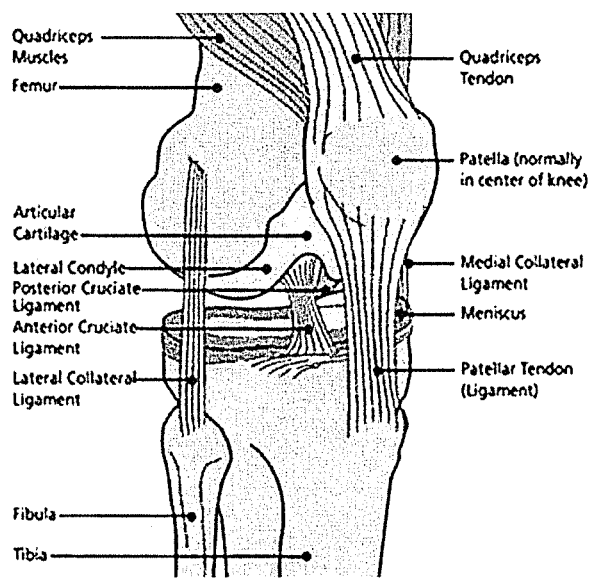
FIG. 1 depicts a knee joint from which a product of the present invention can be made.

As used here, the following definitions and abbreviations apply:

"BTB" means bone-tendon-bone graft obtained from the knee joint and comprising the patella, the patellar tendon, and attached tibial bone block.

"Cartilage product", unless context demands otherwise, means a cartilage product of the instant invention.

"DMEM" means Dulbecco's Modified Eagle Media.

"D-PBS" means Dulbecco's Phosphate Buffered Saline.

"ECM" means extracellular matrix, for example, the matrix of cartilage.

"Examplary" (or "e.g." or "by example") means a non-limiting example.

"Natural", in the context of, for example, "natural ECM" or "natural cartilage", refers to properties exhibited by the ECM or cartilage in its natural state in the donor.

"Partial digestion" (or "limited digestions") means enzymatic digestion wherein one or more digestible sites remain un-digested. In one embodiment, partial digestion is a cell-sparing digestion such that further digestion otherwise decreases cell viability. In one embodiment, digestion can be monitored by any method, e.g. measuring the release of digestion products from a cartilage sample or by the effect of digestion on the physical properties. In one embodiment, a partially digested collagen matrix (e.g. articular cartilage sample) is substantially intact relative to an undigested collagen matrix, for example, the digested collagen matrix retains its shape throughout digestion.

"QC" means Quality Control

"Substantial amount" when used with respect to therapeutic cells (e.g. chondrocytes) and therapeutic bioactive factors (e.g. chondrogenic factors) in a cartilage product means an amount which provides a measurable therapeutic effect in vivo when the cartilage product is administered, e.g. according to the present treatment methods.

The term "devoid" of a substance as used with respect to the present technology includes products that are "substantially free of" or "substantially devoid of" such substance, and includes products that have less than 5% of the substance, more preferably less than 2%, more preferably less than 1%, more preferably less that 0.5%, including 0% of such substance. For example, in some embodiments of the present invention, devoid of subchondral bone, calcified cartilage, or both subchondral bone and calcified cartilage when used with respect to the present technology includes cartilage products which are substantially free of subchondral bone, calcified cartilage or both, cartilage products which are substantially devoid of subchondral bone, calcified cartilage or both, and products that contain less than 5%, less than 2%, less than 1%, less than 0.5% or 0% of subchondral bone, calcified cartilage or both.

Cartilage Products

The present invention provides a cartilage product comprising a collagen matrix having plurality of pores therein. Optionally, the collagen matrix comprises ECM protein fragments, e.g. the collagen matrix is digested hyaline cartilage.

In some embodiments, the cartilage product comprises a matrix having one or more pores therein.

Surprisingly, examplary cartilage products of the present invention support the regeneration of healthy normal articular cartilage by providing type II collagen and proteoglycans, bioactive factors, and viable chondrocytes.

In one embodiment, the cartilage product is flexible. An exemplary flexible cartilage product can be rolled into an arthroscope cannula, can bend extensively without breaking, and can contour to irregular target sites in a subject. Surprisingly, it has been discovered that a flexible cartilage product with viable cells and factors can be produced by appropriately configuring a) the thickness of the collagen matrix; b) extent of poration (pore size and pore density); and c) the extent of digestion.

In one embodiment, the cartilage product comprises viable cells such as chondrocytes. Optionally, the viable cells are native chondrocytes. Optionally, the viable cells are distributed through the collagen matrix in a gradient. Optionally, the pores are aligned with the gradient.

In one embodiment, the ECM protein (e.g. collagen) fragments are substantially shorter than that of native articular cartilage. Additionally or alternatively, a substantial amount of the ECM protein in the collagen matrix is fragmented relative to that of native articular cartilage. Optionally, the ECM protein fragments are produced by partial digestion of a native cartilage, e.g. enzymatic digestion such as collagenase (e.g. Type II) treatment.

In one embodiment, the cartilage product is formulated for cryopreservation, e.g. comprises a cryopreservation medium. Optionally, the cartilage product is cryopreserved.

To illustrate one embodiment of the invention, an examplary cartilage product comprises, as the collagen matrix, a layer (e.g. disk) of hyaline (e.g. articular) cartilage having an array of pores (e.g. channels), wherein the layer of cartilage comprises viable native chondrocytes and collagen fragments produced by partial digestion with a collagen-digesting enzyme such as a collagenase. The layer of cartilage is flexible while retaining its structural integrity. The cartilage product is devoid of subchondral bone and calcified cartilage and comprises a radial layer, a transitional layer, and a tangential layer throughout which a gradient of the viable native chondrocytes are distributed. Optionally, the array of pores are about 0.2 mm to about 2.0 mm (e.g. about 1 mm) in diameter. Optionally, the layer of cartilage comprises about 10 to about 500 pores per $cm^2$ such as about 10 to about 60 pores per $cm^2$. Optionally, the cartilage product is formulated for cryopreservation.

Collagen Matrix

A cartilage product of the present invention comprises a collagen matrix. The collagen matrix can be any extracellular matrix comprising collagen fibrils and bioactive factors. The collagen matrix can be obtained from any source and can be any size and shape. Optionally, the collagen matrix is flexible (e.g. such that it can be rolled or folded and administered via arthroscope cannula).

In one embodiment, the collagen matrix isolated from a subject ('natural collagen matrix') or is grown in-vitro.

In one embodiment, the collagen fibrils comprise type II collagen. Optionally, the collagen matrix is hyaline cartilage such as articular cartilage. Optionally, the articular cartilage is condoyle cartilage, femur condoyle cartilage, tibial plateau cartilage, femoral head cartilage, humoral head cartilage, talus cartilage, or acetabulum cartilage. Optionally, the articular cartilage comprises one or more layers of cartilage selected from: a radial layer, a transitional layer, and a tangential layer.

In one embodiment, the collagen matrix comprises fragmented ECM proteins. Fragmented ECM proteins are optionally produced by partial digestion of a natural collagen matrix. Optionally, the collagen matrix is partially digested with a proteinase such as a collagen-degrading enzyme. Useful collagen-degrading enzymes include, but are not limited to, for example, collagenase (e.g. Types I-IV, bacterial collagenase), other endopeptidases (e.g. trypsin, papain, pepsin), and exopeptidases (e.g. carboxypeptidase).

Figure 16:
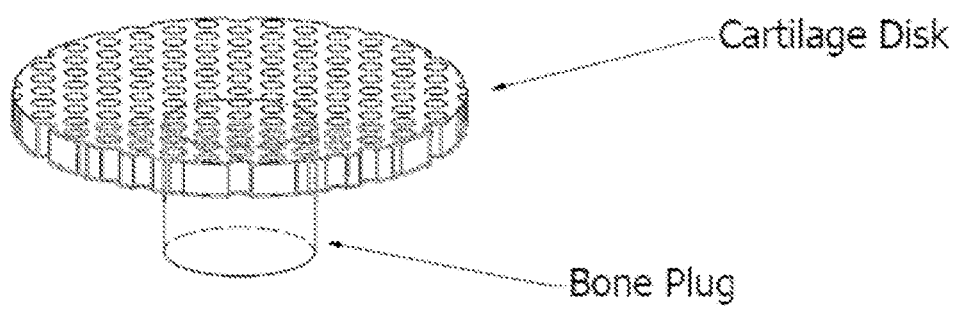
FIG. 16 depicts cartilage products of the present invention comprising a collagen matrix and bone.
Figure 16:
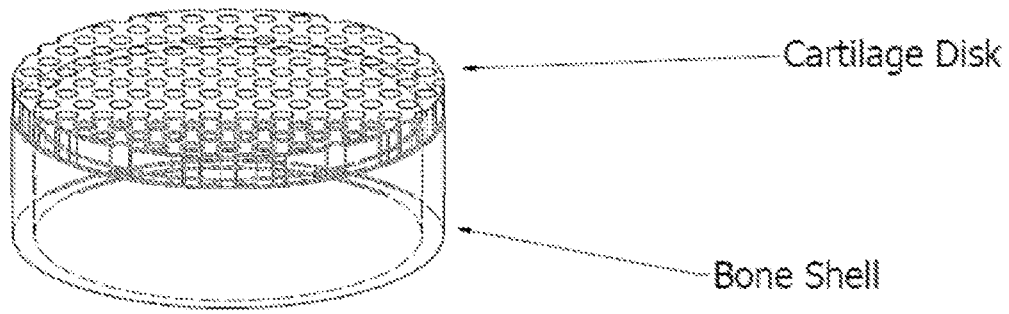

In one embodiment, the collagen matrix is devoid of subchondral bone, calcified cartilage, or both. If present, subchondral bone and calcified cartilage can otherwise inhibit the flexibility of the collagen matrix. In an alternative embodiment, the cartilage product comprises bone, e.g. a reduced-area plug of bone (relative to the collagen matrix) as depicted in FIG. 16A or a shell of bone as depicted in FIG. 16B.

Figure 2:
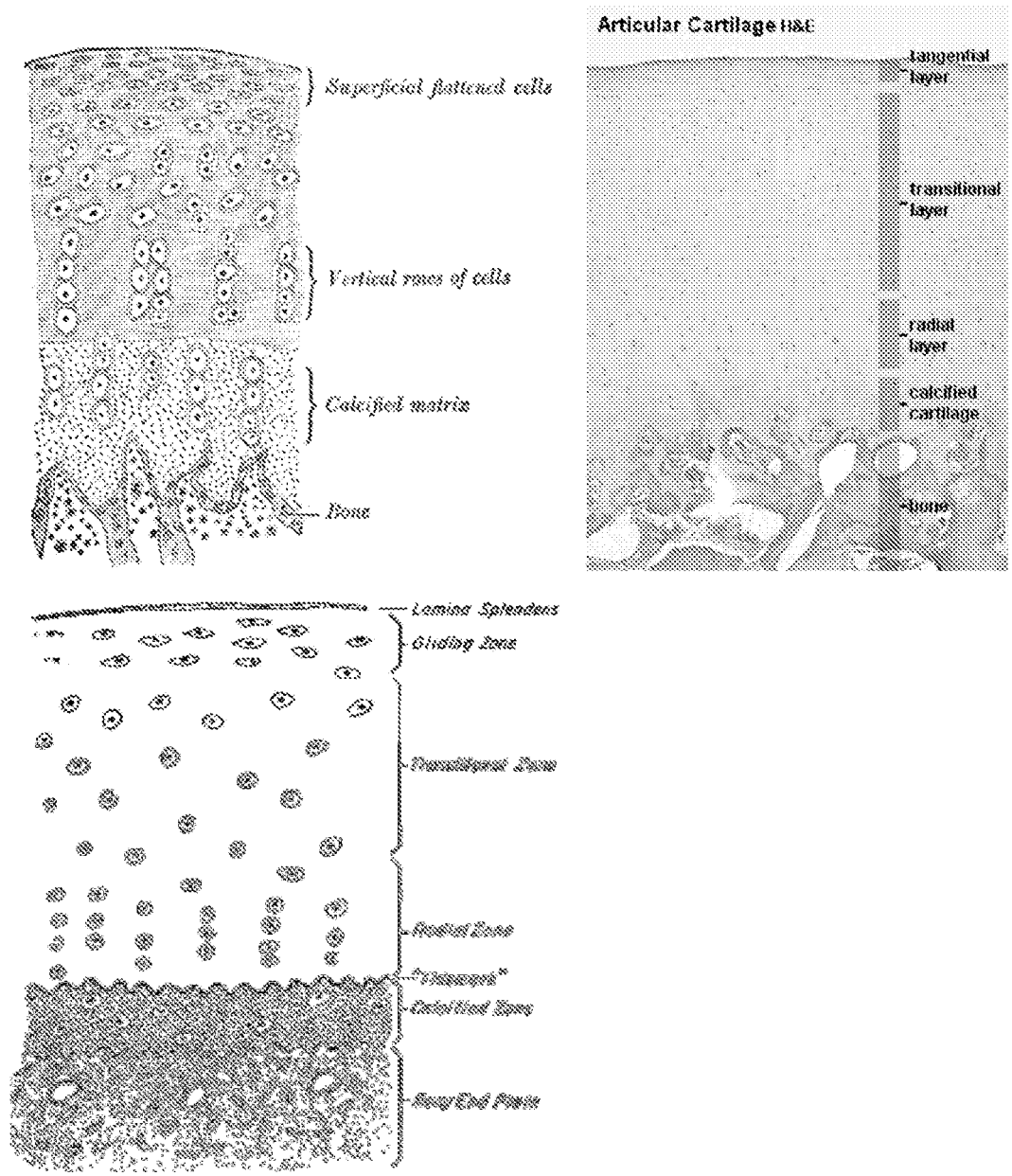
FIG. 2 depicts layers of articular cartilage and adjacent bone of the present invention.

In one embodiment, the collagen matrix is derived from articular cartilage and comprises one or more layers of cartilage selected from: a radial layer, a transitional layer, and a tangential layer. As depicted in FIG. 2, native chondrocytes of a natural articular cartilage are distributed across these layers in a gradient from vertical rows of chondrocytes in the radial layer to flattened cells in the tangential layer. Collagen fibrils of the tangential ('superficial') layer run parallel to the surface. Collagen fibrils in the radial layer are typically oriented towards (e.g. perpendicular to) the articular surface. Collagen fibers in the transitional layer are typically less packed than that of the radial and tangential layers and arranged obliquely or in a more randomized fashion to the articular surface.

Figure 15:
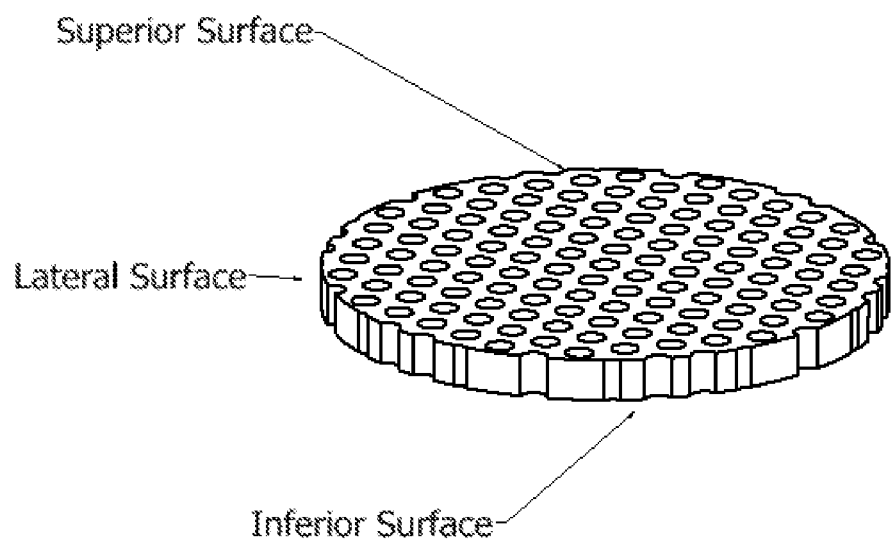
FIG. 15 depicts a cartilage product of the present invention.
Figure 15:
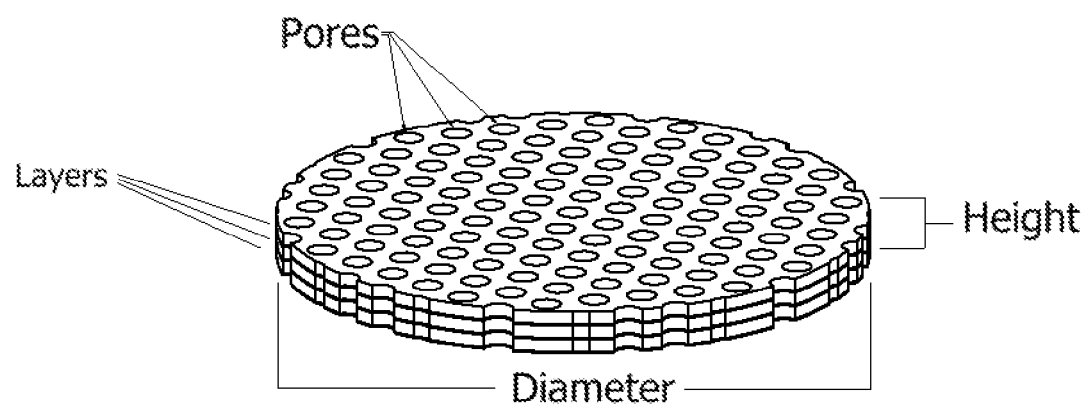

In one embodiment, the collagen matrix has a thickness (or 'height' as depicted in FIG. 15) of less than about 3 mm. Optionally, the collagen matrix has a thickness of about 0.2 mm to about 2 mm or about 1 mm to about 1.5 mm. The thickness can be measured, for example, perpendicular to layers of the collagen matrix (e.g. distance from the surface of a tangential layer to the surface of a radial layer), as depicted in FIG. 15A. Surprisingly, collagen matrices of reduced thickness and tailored porosity can provide a flexible cartilage product that can be administered by arthroscopy and easily contoured to an injured tissue site while retaining its capacity to provide a matrix of viable cells and factors.

In one embodiment, the collagen matrix has a surface (e.g. superior or inferior surface, such as the surface of a tangential layer or a radial layer, respectively) having an area of about 0.5 $cm^2$ to about 5 $cm^2$. Optionally, the collagen matrix has a superior surface and an inferior surface separated by a thickness of less than about 3 mm or less than about 2 mm (e.g. 1 mm to about 1.5 mm).

In one embodiment, the collagen matrix is provided in a round shape (e.g. oval or circle), a rectangular shape, or a square shape. An example of a cartilage product comprising a round collagen matrix is depicted in FIG. 15. Optionally, the width (referred to herein as 'diameter' regardless of shape) of a collagen matrix is greater than the height (referred to herein as 'thickness'), e.g. as depicted in FIG. 15.

In one embodiment, the collagen matrix is a disk, i.e. the diameter (or width) of the collagen matrix surface (e.g.

superior or inferior surface) is greater than the thickness (or height of the lateral surface) of the collagen matrix, e.g. as depicted in FIG. 15. Optionally, the pores are provided in the superior surface, the inferior surface, or both.

Pores

A cartilage product of the present invention comprises a collagen matrix having a plurality of pores. The plurality of pores can be configured in any manner that increases the flexibility of the cartilage and provides a plurality of passageways through which cells and factors can migrate.

The pores can be provided through any surface of the collagen matrix and can extend partially (as in a cavity) or entirely (as in a channel) through the collagen matrix. For example, as depicted in FIG. 15, the pores can be provided through a superior surface, an inferior surface, or both.

According to the present invention, pores in the collagen matrix provided one or more of the following technical features:
 a flexible cartilage product;
 a cartilage product that has superior fixation; and
 a cartilage product that facilitates migration of mesenchymal stem cells (MSCs) and chondrocytes In one embodiment, plurality of pores is configured to impart flexibility to the collagen matrix. By varying the density and size of the pores, one skilled in the art can produce a flexible collagen matrix according to the present invention. Optionally, the plurality of pores have a diameter of about 0.25 mm to about 1.5 mm such as about 0.5 mm to about 1.5 mm (e.g. about 1 mm). Optionally, the collagen matrix comprises a pore density of about 10 to about 500 pores per $cm^2$ such as about 10 to about 100 pores per $cm^2$ or about 10 to about 60 pores per $cm^2$ (e.g. about 36 pores per $cm^2$). Optionally, the collagen matrix comprise a superior or inferior surface having a total pore area from about 3% to about 90% (e.g. about 5% to about 50% or about 10% to about 50%) relative to the total area of said surface. For example, a collagen matrix having pores with a diameter of about 1 mm at 36 pores per $cm^2$ has a pore area of about 28% relative to that of the total area of the surface.

The plurality of pores optionally impart improved fixation. Pores can increase the surface area of the collagen matrix and provide better adhesion, for example, facilitating fixation upon application of an adhesive (e.g. fibrin glue such as Tisseel) or allowing an greater integration into the target site in a subject to which the cartilage product is optionally administered.

The plurality of pores optionally facilitates migration of MSCs and chondrocytes (e.g. donor cells endogenous to the collagen matrix migrating out of the collagen matrix and cells of the implant recipient migrating into the collagen matrix).

In one embodiment, the pores are channels or cavities. A channel is any pore that extends through two faces (e.g. through a superior surface and an inferior surface) of the collagen matrix. A cavity is any pore that does not extend through two faces of the collagen matrix. Optionally, the pores are arranged in an array, e.g. a two dimensional array. Optionally, the collagen matrix comprises one or more cellular or ECM layers (e.g. radial, tangential, or transitional layers) and the pores extend substantially perpendicularly (i.e. 90°±45°) to the layer(s) or diagonally to the layer(s), or the collagen matrix comprises a gradient of cells and the pores are aligned or substantially parallel (i.e. 0°±45°) with the gradient, e.g. as depicted in FIG. 15.

In one embodiment, the collagen matrix comprises a plurality of pores having a diameter selected from: about 0.3 mm to about 2 mm, about 0.5 mm to about 1.5 mm, about 0.8 mm to about 1.2 mm, or about 1 mm.

In one embodiment, the collagen matrix comprises a plurality of pores, wherein about 3% to about 90% of the surface area is porated (e.g. about 3% to about 50% or about 5% to about 50% or about 3% to about 30% or about 5% to about 50%). For example, a collagen matrix comprising cylindrical pores with a 1 mm diameter at a pore density of 36 pores per $cm^2$ would comprise about 28 $mm^2$ of porated surface area per to $cm^2$ of total surface area of the collagen matrix [(0.5 mm pore radius)×($_{TT}$)×(36 pores/$cm^2$)], i.e. 28% porated surface area In one embodiment, the pore size is about 50% to about 150% of the thickness of the collagen matrix or pore length.

Pores can be produced in any manner, for example, mechanical removal of collagen matrix using a drill or tissue punch.

Fragmented ECM

In one embodiment, a cartilage product of the invention comprises fragmented ECM proteins (e.g. the cartilage product comprises a partially digested collagen matrix).

In one embodiment, the fragmented ECM proteins are collagen (e.g. Type II) fragments or proteoglycan fragments. Optionally, the collagen matrix is articular cartilage.

Fragmented ECM proteins can be produced in any manner. Fragmented ECM proteins are optionally produced by partial digestion of a natural collagen matrix (i.e. isolated from a subject). Optionally, the collagen matrix is partially digested with a digestion enzyme (e.g. proteinase) such as, for example, a collagen-degrading enzyme (e.g. collagenase) or a proteoglycan-degrading enzyme (e.g. hyaluranidase).

According to the present invention, partial digestion of a collagen matrix provides one or more of the following technical features:
 a loose ECM that releases and allows migration of cellular factors and viable cells.
 a natural ECM retaining viable native cells
 preservation of physiologic interactions between cells and the ECM
 a clean cartilage product devoid of debris
 a cartilage product comprising ECM fibrils that substantially retain the packing density of natural cartilage
 a cartilage product with greater flexibility
 removes macrophages and reduces immunogenicity A fragmented ECM provides a loose collagen matrix that releases and allows migration of cellular factors and viable cells. For example, cellular (e.g. chondrogenic) factors can leach out into the surrounding micro environment upon administration to a subject. With the teachings provided herein, one skilled in the art can now tailor digestion to provide such a technical feature.

In one embodiment, the fragmentation of ECM is limited to an amount that retains a substantial amount of viable native cells. Upon further fragmentation, the collagen matrix can prematurely release its population of cells before optional administration of the cartilage product. With the teachings provided herein, one skilled in the art can now tailor digestion to provide such a technical feature.

In one embodiment, the ECM is fragmented in a manner that preserves normal interactions between cells and the ECM. For example, the ECM and/or cellular factors therein activate chondrocytes, i.e. induce a shift from the G0 phase to the G1 phase, and also induce MSCs to infiltrate and differentiate into chondrocytes. Without being bound by theory, the inventors believe that these functions enhance therapeutic efficacy.

In one embodiment, the ECM is fragmented in a manner that preserves normal interactions between bioactive factors and the ECM. For example, bioactive factors are retained at levels to greater than about 50% or greater than about 70% compared to predigestion levels.

In one embodiment, the ECM is fragmented in a manner that cleans the cartilage sample of debris. This microscopic and/or macroscopic debris (e.g. ECM fragment) is present in even greater amounts upon poration of a cartilage sample, and can trigger pain and other adverse responses when administered to a subject if the cartilage product of the present technology is not cleansed of debris.

In one embodiment, fragmentation of the ECM is limited to an amount that provides fragmented ECM fibrils that substantially retain the packing density of natural cartilage. Such a technical feature provides a cartilage product having mechanical properties of native cartilage.

In one embodiment, fragmentation of the ECM is limited to an amount that provides a collagen matrix that has any (e.g. each) of the following technical features: is visually intact, is flexible (e.g. such that it can be folded or bent without breaking or rolled to fit in an arthroscope), retains viable native cells, retains non-degraded biofactors (e.g. growth factors), and increases the level of biofactors (e.g. growth factors).

In one embodiment, the cartilage product exhibits greater flexibility with the fragmented ECM compared to that of the same collagen matrix without fragmented ECM. Optionally, the cartilage product is flexible such that it can be inserted into a cannula having a diameter not more than 50% of the diameter (or width) of the cartilage product. For example, the cartilage product in the shape of a disk with a diameter of 2 cm can be flexible enough such that it can be rolled into a cannula of an arthroscope (e.g. a cannula with a diameter of less than about 1 cm).

Viable Chondrocytes

In one embodiment, a cartilage product of the present invention comprises viable chondrocytes. Optionally, the cartilage product is a natural cartilage product (i.e. the collagen matrix is isolated from a subject) and the viable chondrocytes are native, i.e. native to the collagen matrix. Viability can be demonstrated by any means, e.g. through the use of vital stains, phase contrast microscopy, etc.

In one embodiment, the collagen matrix is derived from articular cartilage and comprises viable chondrocytes that are native (or endogenous) to the articular cartilage. Native chondrocytes are distributed across one or more (e.g. all) layers of articular cartilage selected from: a radial layer, a transitional layer, and a tangential layer. The invention alternatively contemplates collagen matrices having exogenous or non-native (i.e. added) chondrocytes. In one embodiment, the collagen matrix comprises viable chondrocytes at its surface. Optionally, at least 70% of the chondrocytes at the surface of the collagen matrix are viable. In some embodiments, the cartilage product comprises at least about 50% viable cells, alternatively at least 60% viable cells. In some embodiments, the cartilage product comprises at least about 70% viable cells, alternatively about 75% viable cells, alternatively about 80% viable cells.

Surface viable cell percentage can be quantified, for example, by microscopy techniques.

In one embodiment, a portion of the chondrocytes is in the $G_0$ phase. Without being bound by theory, the inventors believe that the ECM or ECM factors activate chondrocytes. This activation can be observed as a shift to the $G_1$ phase from $G_0$.

Chondrocytes are thought to be important in maintaining cartilage matrix homeostasis in addition to expressing factors that promote chondrogenesis and cartilage repair. Without being bound by theory, the inventors believe that a superior therapeutic product is obtained by preservation of the cellular and structural organization of native articular cartilage.

Without being bound by theory, the inventors believe that the collagen matrix of cartilage products of the present invention preserves the viability of chondrocytes and extends their life-span ex-vivo (including in the recipient subject). In addition, it is believed that, upon administration to a recipient subject, the collagen matrix can induce the recipient's MSCs to infiltrate the collagen matrix (of the cartilage product) and differentiate into chondrocytes, thereby replenishing the cartilage product with chondrocytes.

As detailed in Example 10, cartilage products of the present invention can contain a substantial amount of viable chondrocytes, even after partial digestion and cryopreservation. A substantial amount of viable chondrocytes is an amount which, when present, enhances the therapeutic efficacy of a cartilage product.

Bioactive Factors

In one embodiment, a cartilage product of the present invention comprises bioactive factors. Optionally, bioactive factors comprise chondrogenic factors. Optionally, the chondrogenic factors include one or more (e.g. each) of TGF-$\beta$1, TGF-$\beta$2, TGF-$\beta$3, BMP-2, BMP-7, bFGF, and IGF-1.

Optionally, the cartilage comprises an extracellular matrix comprising collagen type II, hyaluronan, and aggrecan.

Optionally, the cartilage comprises transcription factors, e.g. Sox5, Sox6, and Sox9.

In one embodiment, the cartilage product comprises TGF-$\beta$1, TGF-$\beta$2, TGF-$\beta$3, BMP-2, BMP-7, bFGF, IGF-1, collagen type II, hyaluronan, aggrecan, Sox5, Sox6, and Sox9.

In one embodiment, the collagen matrix is a natural collagen matrix and the bioactive factors are native to the collagen matrix.

As detailed in Example 16, cartilage products of the present invention can contain bioactive factors (e.g. chondrogenic factors), even after partial digestion and cryopreservation. Additionally or alternatively, cartilage products of the present invention can release bioactive factors when cultured in vivo or in vitro. The amount of a given factor in cartilage product can be determined by a tissue lysate assay, e.g. as detailed in Example 16. The amount of factor released from a cartilage product can be determined by a culture assay, e.g. as detailed in Example 16. For example, as detailed in Example 16 and Table 4, a cartilage product of the present invention can have one or more (e.g. each) of the following technical features:

a. comprises TGF-$\beta$1 in an amount of at least about 11 pg/cm$^2$, for example, about 11 to about 628 pg/cm$^2$.
b. comprises TGF-$\beta$3 in an amount of at least about 4 pg/cm$^2$, for example, about 4 to about 112 pg/cm$^2$.
c. comprises BMP-7 in an amount of at least about 3 pg/cm$^2$, for example, about 3 to about 23 pg/cm$^2$.
d. comprises bFGF in an amount of at least about 169 pg/cm$^2$, for example, about 169 to about 365 pg/cm$^2$.
e. comprises IGF-1 in an amount of at least about 111 pg/cm$^2$, for example, about 111 to about 779 pg/cm$^2$.
f. when cultured, the cartilage product releases TGF-$\beta$1 in an amount of at least about 2617 pg/cm$^2$, for example, about 2617 to about 17818 pg/cm$^2$.

g. when cultured, the cartilage product releases TGF-β2 in an amount of at least about 133 pg/cm$^2$, for example, about 133 to about 623 pg/cm$^2$.

h. when cultured, the cartilage product releases IGF-1 in an amount of at least about 14 pg/cm$^2$, for example, about 14 to about 2842 pg/cm$^2$.

Without being bound by theory, the inventors believe that important to efficient cartilage repair, as facilitated by cartilage products, are growth factors, chondrogenic factors, and other bioactive factors which mediate extracellular matrix production and promote chondrogenesis in vivo. For example, TGF-β1-3 promote chondrogenic differentiation and regulate collagen expression; BMP-2 and BMP-7 Induce chondrogenesis of MSCs and stimulate ECM production by chondrocytes; bFGF stimulates proliferation of chondrocytes; IGF-1 induces ECM synthesis; and ECM (Collagen, Hyaluronan, and Aggrecan) mediates mechanical regulation of chondrogenesis.

Formulation

According to the present invention, the cartilage product is optionally formulated with a cryopreservation medium.

In one embodiment, the cryopreservation medium comprising one or more cell-permeating cryopreservatives, one or more non cell-permeating cryopreservatives, or a combination thereof.

Optionally, the cryopreservation medium comprises one or more cell-permeating cryopreservatives selected from, but not limited to, for example, DMSO, a glycerol, a glycol, a propylene glycol, an ethylene glycol, or a combination thereof.

Optionally, the cryopreservation medium comprises one or more non cell-permeating cryopreservatives selected from, but not limited to, for example, polyvinylpyrrolidone, a hydroxyethyl starch, a polysaccharide, a monosaccharides, a sugar alcohol, an alginate, a trehalose, a raffinose, a dextran, or a combination thereof.

Other examples of useful cryopreservatives are described in "Cryopreservation" (BioFiles Volume 5 Number 4-Sigma-Aldrich® datasheet).

In one embodiment, the cryopreservation medium comprises a cell-permeating cryopreservative, wherein the majority of the cell-permeating cryopreservative is DMSO. Optionally, the cryopreservation medium does not comprise a substantial amount of glycerol.

In one embodiment, the cryopreservation medium comprises DMSO, e.g. in an amount of about 1% to about 50% DMSO by volume (e.g. about 10%).

In one embodiment, the cryopreservation medium comprises additional components such as albumin (e.g. HSA or BSA), an electrolyte solution (e.g. Plasma-Lyte, PBS, or saline), or a combination thereof In one embodiment, the cryopreservation medium comprises 1% to about 20% albumin (e.g. HSA) by weight and about 1% to about 50% cryopreservative by volume (e.g. about 10%) such as DMSO.

Non-Immunogenicity

In one embodiment, the cartilage product is substantially non-immunogenic.

Cartilage products of the present invention have one or more technical features that reduce immunogenicity. Examples of such technical features include:

Absence of non-sequestered cells
Presence of immunoprivileged MSC cells and low levels of circulating immunogenic cells and TNF-α.
Selective killing by cryopreservation As taught herein, certain embodiments of the present invention comprise a collagen matrix having viable cells such as chondrocytes that are native to the collagen matrix. The invention also contemplates cartilage products having non-native cells such as chondrocytes added to the matrix. While exogenous (and endogenous) chondrocytes are a potential source of immunogenicity, cartilage products of the present invention exhibit surprisingly low or absent immunogenicity. Without being bound by theory, the inventors believe that chondrocytes (especially native chondrocytes), which are embedded in the collagen matrix, are more effectively sequestered from the surrounding environment in a subject to which the cartilage product is administered, thereby reducing immunogenicity.

In one embodiment, the cartilage product has depleted levels of circulating immunogenic cells and TNF-α. Optionally, such a cartilage product substantially lacks a response to lipopolysaccharide (LPS). Such a cartilage product can be provided, for example, by performing manufacturing steps of washing/rinsing, digestion, cryopreservation, or any combination thereof.

Manufacture

A cartilage product can be produced in any manner. In one embodiment, the invention provides a method of making a cartilage product comprising providing a cartilage sample, porating the cartilage sample; and partially digesting the cartilage sample.

In one embodiment, the method comprises removing subchondral bone and/or calcified cartilage from the cartilage sample.

In one embodiment, the method comprises cryopreserving the cartilage sample after said steps of porating and partial digestion. Optionally, the step of cryopreservation comprises cryopreserving in a manner that spares viable cells.

In one embodiment, the step of partial digestion is performed in a manner that retains a substantial amount of viable cells.

In one embodiment, the cartilage sample is porated to an extent that increases flexibility of the cartilage sample.

In one embodiment, processing of the cartilage sample is performed in a manner that does not generate a substantial amount of heat. Optionally, cutting of cartilage tissue comprises the use of a low-speed saw or drill and/or a tissue punch.

In one embodiment, the process comprises chilling (e.g. continually or periodically) the cartilage sample.

Cartilage Sample

The cartilage sample can be obtained from any source and can be provided in any shape, thickness, and surface area. Optionally, the source is a subject such as a human subject. Optionally, the source is a cadaver.

In one embodiment, the cartilage sample is any cartilage sample comprising type II collagen. Optionally, the cartilage sample is selected from: hyaline cartilage, fibrocartilage, and elastic cartilage.

In one embodiment, the cartilage sample comprises hyaline cartilage. Optionally, the cartilage sample is an articular cartilage sample (e.g. obtained from a donor bone). Optionally, the cartilage sample is isolated (i.e. separated) from subchondral bone and/or calcified cartilage. Cartilage can be separated from subchondral bone after removing a cartilage sample in the form of an osteochondral plug (e.g. using a tissue punch) or the cartilage can be separated directly from subchondral bone while present on the donor bone (e.g. by slicing off cartilage from the donor bone). Other useful hyaline cartilages include nasal cartilage, tracheal cartilage, and laryngeal cartilage.

In one embodiment, the cartilage sample is articular cartilage. Articular cartilage can be obtained from any donor bone. Optionally, the cartilage sample is obtained from long bones such as femur, tibia, fibula, humerus, ulna, radius, or short bones such as the bones of the hands or feet (e.g. talus), flat bones such as pelvic bones (e.g. acetabulum), irregular bones such as vertebrae, and sesamoid bones. Articular cartilage can be obtained from the condoyle of any bone. Optionally, the cartilage sample is obtained as a plug (e.g. 1 cm or 2 cm plug). Optionally, the cartilage sample is removed of subchondral bone and/or calcified cartilage.

In one embodiment, the cartilage sample comprises fibrocartilage. Optionally, the cartilage sample is obtained from a source selected from: pubic symphysis, annulus fibrosis, intervertebral disc, meniscus, and temporomandibular joint.

In one embodiment, the cartilage sample comprises elastic cartilage. Optionally, the cartilage sample is obtained from a source selected from ears, larynx, and epiglottis.

In one embodiment, the cartilage sample is obtained from a mammal, an ungulate, an organism of the Sus genus, a pig, a primate, a higher primate, or a human.

In one embodiment, the cartilage sample is screened for thickness. Optionally, the thickness is 0.2 mm to about 2.0 mm such as about 1 mm to about 1.5 mm. For example, cartilage samples that are thinner than the minimum thickness can be discarded while cartilage samples that are thicker than the maximum thickness are trimmed down to size. Surprisingly, by reducing the thickness of the cartilage sample and porating the cartilage sample, a flexible cartilage product is obtained that easily contours to an injured tissue site while retaining the capacity to provide a matrix of viable cells and bioactive factors.

In one embodiment, the collagen sample has a surface (e.g. upper ("superior") or lower ("inferior") surface) having an area of about 0.5 $cm^2$ to about 5 $cm^2$. Optionally, the collagen sample has an upper surface and a lower surface separated by a thickness of less than about 3 mm (e.g. 1 mm to about 1.5 mm).

In one embodiment, the collagen sample is provided in a round shape (e.g. oval or circle), a rectangular shape, or a square shape.

In one embodiment, obtaining the cartilage sample comprises chilling the sample, e.g. using chilled solvent, a cold room, a cold plate. In one embodiment, obtaining the sample comprises isolating without generating a substantial amount of heat, e.g. using a low speed saw. In some embodiments, chilling comprises the use of an ice water bath.

Poration

A method of producing a cartilage product of the present invention comprises a step of porating a cartilage sample. The poration can be conducted in any manner that increases the flexibility of the cartilage and provides a plurality of passageways through which cells and factors can migrate.

In one embodiment, the cartilage is porated using laser poration or mechanical proration.

In one embodiment, the cartilage is porated using mechanical proration. Optionally, the mechanical poration is provided by drilling, punching, hydraulic poration (e.g. high pressure fluid drilling), or combinations thereof. Optionally, the cartilage is porated using a single punch or a multi-punch device.

In one embodiment, the cartilage sample is porated to an extent that increases flexibility of the cartilage sample. Optionally, the cartilage sample is porated to provide pores having a diameter of about 0.25 mm to about 2 mm (e.g. about 0.25 mm to about 1.5 mm or about 0.5 mm to about 1.5 mm) in diameter. Optionally, the cartilage sample is porated to provide about 10 to about 400 pores per $cm^2$ such about 10 to about 100 pores per $cm^2$ or about 20 to about 60 pores per $cm^2$ (e.g. about 36 pores per $cm^2$). Optionally, the cartilage sample comprises a layer of cartilage and the pores pass through the majority (e.g. entirety) of the layer of cartilage.

In one embodiment, the cartilage sample is porated to an extent of about 10 $mm^2$ to about 50 $mm^2$ of porated surface area per $cm^2$ of surface area of the cartilage sample. For example, a collagen matrix comprising cylindrical pores with a 1 mm diameter at a pore density of 36 pores per $cm^2$ would comprise about 28 $mm^2$ of porated surface area per $cm^2$ [(0.5 mm pore radius)$\times(_{TT})\times$(36 pores/$cm^2$)].

In one embodiment, porating the cartilage sample comprises chilling (e.g. continually or periodically) the sample, e.g. using chilled solvent and/or a cold room or a cold plate. In one embodiment, porating the cartilage sample comprises porating the cartilage sample without generating a substantial amount of heat, e.g. using a low speed drill or a tissue punch.

Digestion

A cartilage product of the invention can be produced by partially digesting a cartilage sample, e.g. using a digestive enzyme such as a proteinase or proteoglycan digesting enzyme.

According to manufacturing methods of the present invention, a step of partial digestion modifies the ECM of the cartilage sample and can be performed in a manner that provides one or more of the following technical features:

a loose ECM that releases and allows migration of cellular factors and viable cells.

a natural ECM retaining viable native cells preservation of physiologic interactions between cells and the ECM a clean cartilage product devoid of debris a cartilage product comprising ECM fibrils that substantially retain the packing density of natural cartilage a cartilage product with greater flexibility removes macrophages and reduces immunogenicity In one embodiment, the step of partial digestion is performed in a manner that loosens the ECM, e.g. cleaving peptide bonds within collagen. A loose ECM releases and allows migration of cellular factors and viable cells. For example, bio- (e.g. chondrogenic) factors can leach out into the surrounding micro environment upon administration to a subject. With the teachings provided herein, one skilled in the art can now tailor digestion to provide such a technical feature.

In one embodiment, the step of partial digestion is performed in a manner that retains a substantial amount of viable native cells, for example, by limiting digestion to a cell-sparing amount. With the teachings provided herein, one skilled in the art can now tailor digestion to provide such a technical feature.

In one embodiment, the step of partial digestion is performed in a manner that preserves normal interactions between cells and the ECM. For example, the ECM and/or cellular factors therein activate chondrocytes, i.e. induce a shift from the G0 phase to the G1 phase, and also induce MSCs to infiltrate and differentiate into chondrocytes. Without being bound by theory, the inventors believe that these functions enhance therapeutic efficacy.

In one embodiment, the step of partial digestion is performed in a manner that cleans the cartilage sample of debris. This microscopic and/or macroscopic debris (e.g. ECM fragment) is present in even greater amounts upon poration of a cartilage sample, and can trigger pain and other adverse responses when administered to a subject if the cartilage product of the present technology is not cleansed of debris.

In one embodiment, the step of partial digestion is performed in a manner that provides fragmented ECM fibrils that substantially retain the packing density of natural cartilage. For example, partial digestion can be limited to an amount that does not destroy the structural integrity of the cartilage sample. Such a technical feature provides a cartilage product having mechanical properties of native cartilage, for example, to provide a long lasting, weight-bearing cartilage graft.

In one embodiment, the step of partial digestion is performed in a manner that imparts flexibility to the cartilage product.

In one embodiment, the cartilage sample is digested using a collagen-digesting enzyme (e.g. collagenase or cathepsin) or a proteoglycan-digesting enzyme (e.g. hyaluronidase, aggrecanase, or papain). Optionally, the cartilage sample is digested in a manner that retains cell-matrix interaction. For example, trypsin digestion is typically performed with a chelator such as EDTA to sequester magnesium and calcium, which otherwise inhibit the action of trypsin. Such chelators can dissociate cells from the matrix. Indeed, trypsin itself can cut matrix proteins to which cells adhere or attach. Accordingly, one embodiment of the invention contemplates the use of non-dissociative digests that can partially digest a cartilage sample in a manner that retains native cells such as chondrocytes.

In one embodiment, the step of partial digestion comprises digesting collagen II in a cartilage sample (e.g. articular cartilage). Digestion enzymes which are useful in the partial digestion of type II collagen matrices include: collagenase (e.g. Type II, any of collagenase I-IV, and bacterial collagenase), other endopeptidases (e.g. trypsin, papain, pepsin), and exopeptidases (e.g. carboxypeptidase).

In one embodiment, partial digestion comprises non-enzymatic digestion, for example, steam-based, acid-based, or fenestration-based digestion. Optionally, the non-enzymatic digestion is mechanical digestion, e.g. partial mincing or fenestration-based digestion.

In some embodiments, the cartilage products of the present invention are not digested. In other embodiments, the cartilage products of the present invention are partially digested by digestive means including enzymatic (e.g. collegenase, pronase, proteinase K, etc. treatment), biochemical (e.g. papain), thermal (e.g. increased heat), chemical (keratin sulfate, tosyllysylchloromethane), mechanical (perforated), any other means of digestion known by those of skill in the art, and combinations of any two or more of the foregoing.

Cryopreservation

A cartilage product of the present invention may be used fresh or may be preserved for a period of time. Optionally, the cartilage product is subjected to a freeze-thaw cycle, i.e. cryopreserved and then thawed.

In one embodiment, a cartilage product is cryopreserved. A cartilage product may be cryopreserved by incubation at freezing temperatures (e.g. at −80° C.±5° C.) in a cryopreservation medium.

In one embodiment, cryopreservation can comprise a controlled method of freezing, i.e. wherein the cartilage product is held at one or more temperatures intermediate of room temperature and −80° C. Cryopreservation can comprise, for example, incubating the cartilage product at 4° C. for 30 min to 24 hrs (e.g. about 30 to about 90 min), then incubating the cartilage product at about −20° C. to about −40° C. (e.g. about −30° C.) for about 20 min to about 12 hrs (e.g. about 20 to about 60 min) and then incubating at −80° C. until use for example, by reducing the temperature at a rate of about 4° C./min to about −80° C./min. Alternatively, the cartilage product can be rapidly frozen at −80° C. or snap frozen in liquid nitrogen.

The cartilage product may then be thawed for use. Optionally, the cartilage product is cryopreserved in a manner such that cell viability is retained surprisingly well after a freeze-thaw cycle.

In one embodiment, cryopreservation comprises storage in a cryopreservation medium comprising one or more cell-permeating cryopreservatives, one or more non cell-permeating cryopreservatives, or a combination thereof. Optionally, the cryopreservation medium comprises one or more cell-permeating cryopreservatives selected from DMSO, a glycerol, a glycol, a propylene glycol, an ethylene glycol, or a combination thereof. Optionally, the cryopreservation medium comprises one or more non cell-permeating cryopreservatives selected from polyvinylpyrrolidone, a hydroxyethyl starch, a polysaccharide, a monosaccharides, a sugar alcohol, an alginate, a trehalose, a raffinose, a dextran, or a combination thereof. Other examples of useful cryopreservatives are described in "Cryopreservation" (BioFiles Volume 5 Number 4—Sigma-Aldrich® datasheet).

In one embodiment, the cryopreservation medium comprises a cell-permeating cryopreservative, wherein the majority of the cell-permeating cryopreservative is DMSO.

In one embodiment, the cryopreservation medium comprises DMSO, e.g. about 1% to about 50% DMSO by volume (e.g. about 10%).

In one embodiment, the cryopreservation medium comprises additional components such as albumin (e.g. HSA or BSA), an electrolyte solution (e.g. Plasma-Lyte), or a combination thereof In one embodiment, the cryopreservation medium comprises 1% to about 20% albumin by weight and about 1% to about 50% cryopreservative by volume (e.g. about 10%). Optionally, the cryopreservative comprises DMSO (e.g. in a majority amount).

Antiseptic Treatment

A cartilage product of the present invention is optionally treated with one or more antiseptic solutions to reduce bioburden. Optionally, the cartilage product is treated with (e.g. incubated in) an antibiotic. Optionally, the cartilage product is treated (e.g. wiped down) with povidone-iodine.

In some embodiments, the cartilage product is treated with an antibiotic, where the antibiotic is gentamicin sulfate (Abraxis Pharmaceutical Products, Schaumburg, IL), vancomycin HCI (Hospira Inc., Lake Forest, IL), and/or amphotericin B (Sigma Aldrich, St. Louis Mo.).

Optionally, the cartilage product is treated with a fungicidal solution.

Screening for Cells, Viability, and Chondrogenic Factors

In one embodiment, a cartilage product is screened for chondrocytes, cell viability, and one or more structural or functional components such as bioactive factors and other ECM components (e.g. chondrogenic factors).

Through the insight of the inventors, it has been discovered that certain components correlate with therapeutic efficacy.

In one embodiment, the components screened for include one or more of the bioactive factors listed in Table 4, the presence of viable chondrocytes, or a combination thereof.

Miscellaneous

In one embodiment, a method of manufacturing a cartilage product of the present invention comprises treating the cartilage product with one or more solutions. Optionally, the pH of the one or more solutions ranges from 5-10. Optionally, treatment solutions comprise one or more of: saline, PBS, Plasmalyte, and water.

Methods of Use

In one embodiment, a cartilage product of the present invention is used to treat an injured tissue in a subject. The injured tissue can be any injured tissue. A method of treatment may be provided, for example, by administering to a subject in need thereof, a cartilage product of the present invention.

In one embodiment, the injured tissue is cartilage. Optionally, the injured tissue is articular cartilage. Optionally, the method comprises removing injured cartilage at and administering the cartilage product to the site at which the injured cartilage was removed. Optionally, the step of removing comprises removing a plug comprising the injured tissue and the cartilage product is cut or shaped (or both) to fit the void left by removing the plug (e.g. 2 cm diameter plug is removed and replaced with a 2 cm diameter cartilage product in the shape of said plug).

In one embodiment, the injured tissue is articular cartilage and the method further comprises microfracturing the injured tissue site, e.g. removing damaged articular cartilage followed by physically insulting the underlying subchondral bone to exposed bone marrow and create bleeding. Optionally, the cartilage product is placed on the subchondral bone after microfracturing.

Microfracturing is a technique that can stimulate healing by forming a blood clot, thereby introducing inflammatory cytokines, growth factors and MSCs. Microfracturing alone results in the formation of fibrocartilage comprising collagen type I and has poor biomechanical performance and abnormal bone growth resulting in osteoarthritis. Surprisingly, through the insight of the inventors, it has been discovered that the present cartilage products overcome these deficiencies by providing a type II collagen matrix with viable chondrocytes to promote chondrogenesis of the MSCs introduced by microfracturing.

In one embodiment, a cartilage product of the present invention is administered arthroscopically. Surprisingly, a flexible cartilage product of the invention can be easily administered arthroscopically (i.e. is flexible such that it can be administered through an arthroscope cannula) and adapts to contours at the site of administration, e.g. contours of chondral surfaces.

In one embodiment, a cartilage product is fixed at the site of administration. Optionally, the cartilage product if fixed by an adhesive (e.g. fibrin glue) or by a mechanical device (e.g. a pin such as a bioresorbable pin).

Surprisingly, through the insight of the inventors, cartilage products of the present invention provide greater healing and can be used to treat injuries of larger sizes.

Surprisingly, through the insight of the inventors, cartilage products provide a collagen matrix with native mechanical and functional properties that is efficiently integrated into the cartilage at the target site. Without being bound by theory, it is believed that the superior healing capacity of cartilage products taught herein is due, in part to complex interactions between the donor matrix (cartilage product), donor cells, recipient (treated subject) cells, and recipient matrix. This is far superior to prior therapies such as autologous chondrocyte implantation which are typically only palliative.

EXAMPLES

Example 1 Isolation of Femoral Condyles and Tibial Plateau

A human knee joint was obtained, as depicted in FIG. 1.

The outer surfaces of the knee joint were cleaned with iodine (10% povidione-iodine solution, Purdue, "Betadine") without contacting the cartilage with iodine. The knee joint was dissected to separate the femur, tibia and fibula without damaging the cartilage surfaces. Soft tissue (adipose, muscle, fascia, ligaments and tendons) were removed to expose the articular cartilage surfaces on tibial plateau and femoral condyles.

The portions containing the articular cartilage (tibial plateau and the condyles of the femur) were chilled by placing in chilled saline (0.9% Sodium Chloride irrigation solution, USP) on a cold plate.

Example 2 Isolating Cartilage Plugs

Femur condoyles and tibial plateau were obtained as detailed in Example 1. Osteochondral plugs having diameters of about 1cm or about 2 cm were obtained from the femur condoyles and tibial plateau. During isolation of the plugs, the condoyles and tibial plateau were kept moist and chilled by periodic immersion in chilled saline or wiped with a wipe soaked in chilled saline. The isolated plugs were then chilled by placement in chilled saline.

The osteochondral plugs were obtained using a tissue punch while avoiding any areas of damaged cartilage. Specifically, tissue punches with diameters of 1 cm or 2 cm were used to remove whole plugs of cartilage and underlying bone from the articular surface.

Example 3 Isolating a Cartilage Sample from Subchondral Bone and Calcified Cartilage Osteochondral plugs were obtained as detailed in Example 2. The subchrondral bone and calcified cartilage was removed from the osteochondral plugs to provide cartilage samples in the form of cartilage disks. During this process, the cartilage was chilled periodically with chilled saline to prevent overheating.

Specifically, each osteochondral plug was held securely and the subchondral bone layer was cut (removed) using a sagittal saw with a bent angle blade from the layer of cartilage. Once the subchondral bone was removed, any remaining bone and calcified cartilage was shaved from the underside of the cartilage discs. To prevent overheating, the tissue was frequently immersed in chilled saline throughout the sawing and shaving process. This process was repeated for each of the cartilage disks.

Example 4 Sizing of Cartilage Samples

Isolated cartilage samples in the form of cartilage disks were obtained as detailed in Example 3, and then sized to increase their flexibility. The thickness of cartilage samples was measured using a caliper or disc thickness gauge. Disks that were thicker than about 1.5 mm were trimmed down to about 1.5 mm. Disks thinner than about 1 mm were discarded.

Example 5 Porating a Cartilage Sample

Cartilage samples (cartilage disks) were obtained and sized as detailed in Example 4 and then porated to provide a cartilage layer (disk) having pores of about 1mm in diameter with a pore density of about 36 pores/cm² as depicted in FIG. 15.

Specifically, a pore pattern (a perforated stainless steel screen) was placed over the cartilage sample and a 1 mm biopsy punch was used to punch out the pores (holes) of cartilage through the pattern. The porated cartilage sample was then chilled by immersion in chilled saline.

Example 6 Partial Digestion of a Cartilage Sample

Cartilage samples (cartilage disks) were obtained as detailed in Example 5 and then digested with Type II collagenase.

Specifically, the collagenase was formulated in DMEM (200 units/ml of collagenase type II, Sigma). The porated cartilage samples were incubated in the collagenase suspension for 30±2 minutes at 37° C.±2° C. The collagenase solution was removed and the disks were rinsed with chilled saline.

Example 7 Antibiotic Treatment of a Cartilage Product

Cartilage samples (cartilage disks) were obtained as detailed in Example 7 and then incubated antibiotic solution containing of gentamicin sulfate (50 µg/mL; Abraxis Pharmaceutical Products, Schaumburg, IL), vancomycin HCl (50 µg/mL; Hospira Inc., Lake Forest, IL), and amphotericin B (2.5 µg/mL; Sigma Aldrich, St. Louis, MO) in DMEM at 37° C.±2° C. for 18 hrs to 48 hr. Following the incubation, the antibiotic solution was removed and the disks were rinsed in chilled saline.

Example 8 Cryopreservation

Cartilage products were obtained as detailed in Example 8 and cryopreserved in a cryopreservation solution.

The cryopreservation solution contained 10% dimethyl sulfoxide (DMSO) (Bioniche Teo. Inverin Co) and 5% human serum albumin (HSA; Baxter) in PlasmaLyte-A (Baxter Healthcare Corp.).

For each cartilage product, a vial was filled with about 7 ml of the cryopreservation solution and a cartilage product was transferred into the vial using forceps. The cartilage product was wiped to remove any residual liquid (e.g. saline solution) prior to placement in the cryopreservation solution. A stopper was placed in the vial containing the cryopreservation solution and the cartilage product.

The vial was sealed after capping, crimping, and bagging the vial, and then cryopreserved at about −80° C. by placing the vial in an automated freezer. The freezer was programed to reduce the temperature in a gradual and step-wise manner using the following temperature program:

| | |
|---|---|
| Step 1 | reduce temperature to 4° C. at 4.0° C./m |
| Step 2 | hold temperature for 60 m at 4° C. |
| Step 3 | reduce temperature to −30° C. at 1.0° C./m |
| Step 4 | hold temperature at −30° C. Hold for 30 m |
| Step 5 | reduce temperature to −80° C. at 4.0° C./m |
| Step 6 | hold temperature at −80° C. |

Example 9 Cartilage Product

Cartilage products were made by a method of the present invention, specifically isolating, porating, digesting, and cryopreserving a cartilage sample using the method detailed in Example 1 through Example 8. The cartilage products had a natural structural organization and promote proper articular cartilage repair. Surprisingly, these therapeutically active cartilage products produced by the methods taught herein had the following technical features:
- contain viable native chondrocytes having a capacity for chondrogenesis
- contain bioactive factors
- are non-immunogenic
- provide a flexible repair matrix having a natural structural organization Example 10 Viable Chondrocytes After Cryopreservation Using Various Freezing Methods Cartilage products from Example 9 were analyzed for viable chondrocytes after cryopreservation.

Various freezing methods were investigated to determine their effect on cell viability. Cartilage products were formulated in a cryopreservation medium comprising 10% Dimethyl Sulfuric oxide (DMSO) and 5% Human Serum Albumin (HSA) in plasmalyte-A (sodium chloride, sodium gluconate, sodium acetate, potassium chloride and magnesium chloride).

In a first set of experiments, different cryopreservation methods were tested to determine the effect on preservation viable cells within the cartilage product.

Method 1: Hold the cartilage product at 4° C. to allow time for equilibration (i.e. penetration of cryosolution into the tissue), followed by placing the product in a styrofoam box and freezing in a −80° C. freezer which results in a uniform cooling rate of about −0.5° C./min.

Method 2, Step:
1. Reduce the temperature in a step-wise manner:
2. reduce temperature to 4° C. at 4.0° C./m
3. hold temperature for 60 m at 4° C. for equilibration
4. reduce temperature to −30° C. at 1.0° C./m
5. hold temperature at −30° C. Hold for 30 m
6. reduce temperature to −80° C. at 4.0° C./m
7. hold temperature at −80° C.

To demonstrate the presence of viable cells, the cartilage products were stained using a LIVE/DEAD® Viability/Cytotoxicity kit (Molecular Probes Inc., Eugene, OR) to qualitatively assess cell viability. Staining was performed as per the manufacturer's protocol. Thin portions of cartilage products (e.g. approximately 0.5 cm×0.5 cm×0.02 cm) were thawed in a 37° C. water bath and used for analysis. Evaluation of stained tissue was performed using a fluorescence microscope. An intense uniform green fluorescence indicated the presence of live cells, and a bright red fluorescence indicated the presence of dead cells.

Figure 3:
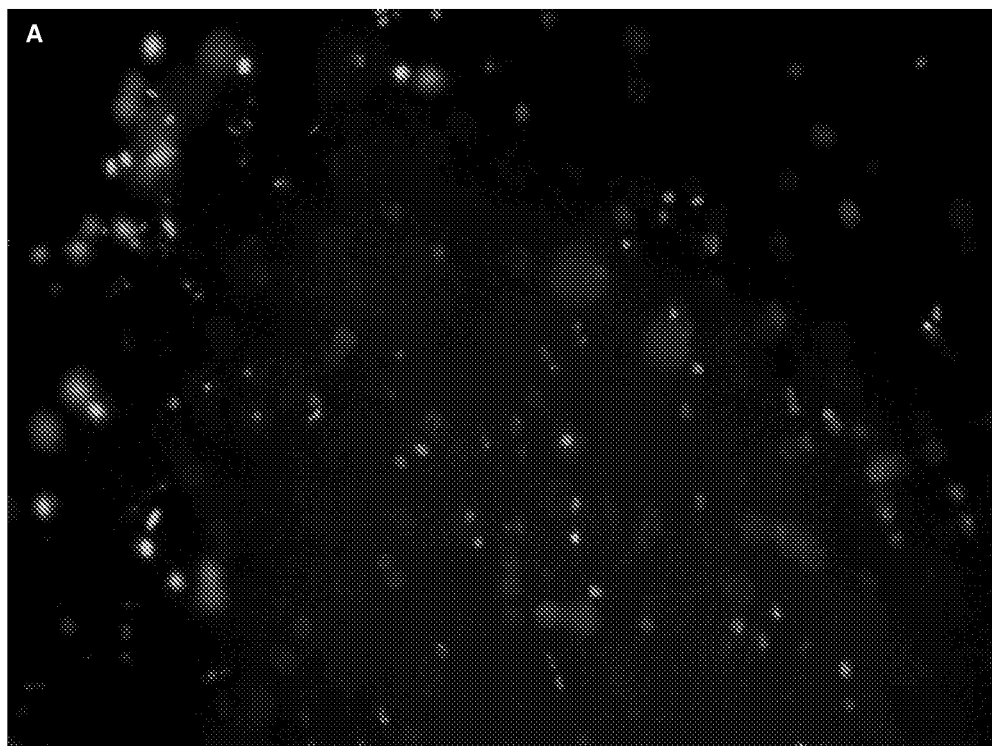
FIG. 3 depicts viable chondrocytes in cryopreserved cartilage products of the present invention.
Figure 3:
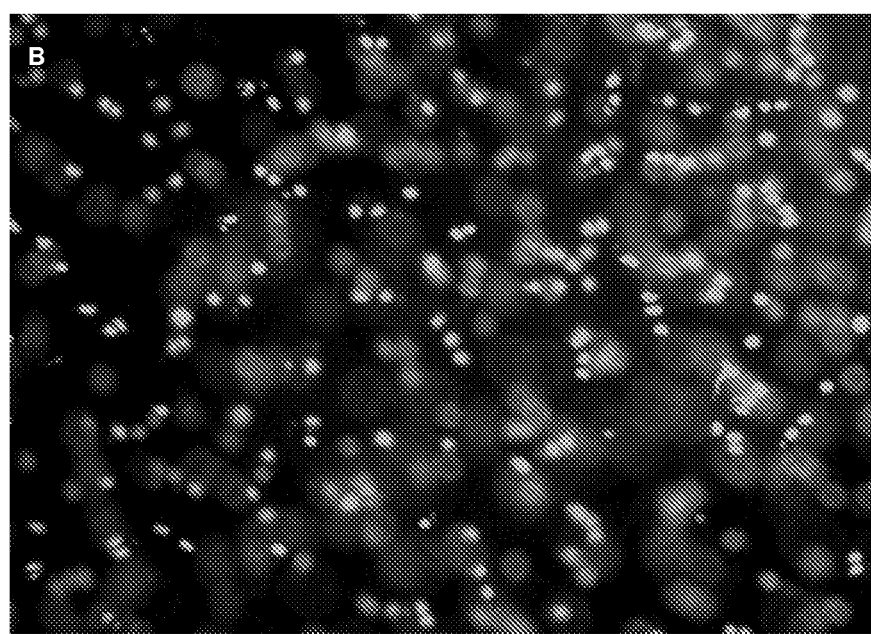

As depicted in FIG. 3, cartilage products cryopreserved by the stepwise method (Method 2; FIG. 3b) comprise enhanced levels of viable chondrocytes relative cartilage products cryopreserved using a method comprising a single equilibration step followed by gradual cooling (Method 1; FIG. 3a). Chondrocytes are the predominant cell type present within articular cartilage and are integral in maintaining cartilage matrix homeostasis. Additionally, chondrocytes express factors that promote chondrogenesis and cartilage repair. It is quite surprising that viable chondrocytes remain following cryopreservation as several attempts have been cited in the literature to cryopreserve cartilage with little success in preserving viable cells once thawed (e.g. Acosta et al, 2007. *Clin Orthop Relat Res*; 460:234-9).

Figure 4:
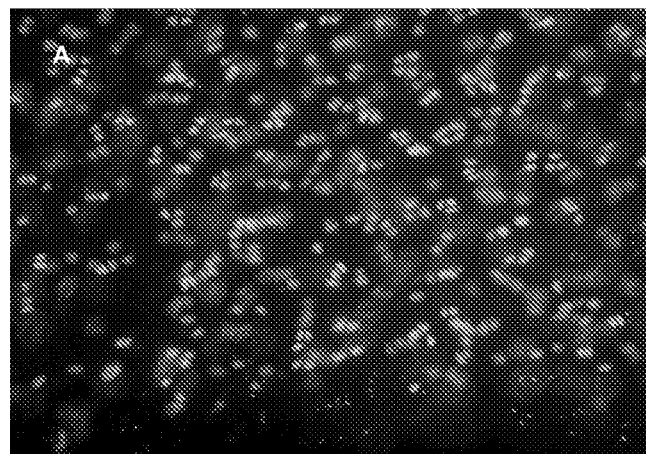
FIG. 4 depicts viable chondrocytes in cryopreserved cartilage products of the present invention.
Figure 4:
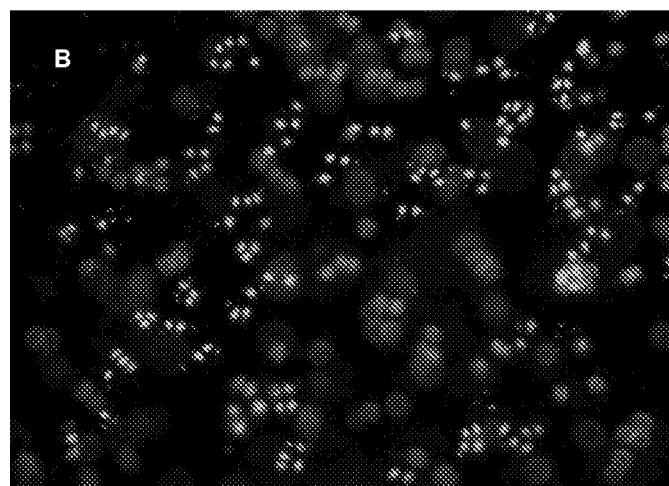
Figure 4:
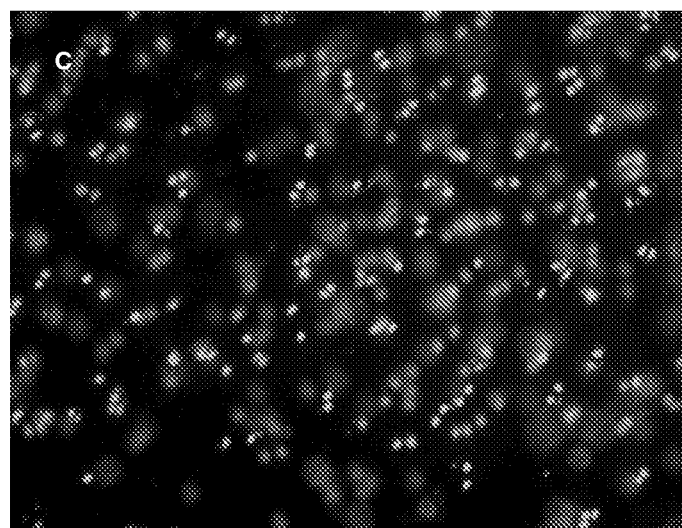

In a second set of experiments, the duration of equilibration was tested for its effect on the level of viable chondrocytes in thawed cartilage products. Specifically, cell viability was accessed after cryopreservation using method 2 (FIG. 4a) and compared to methods of cryopreservation that substituted a 2 hour equilibration step (FIG. 4b) or 4 hour equilibration step (FIG. 4c) for the 1 hour equilibration step at 4° C. Surprisingly, as depicted in FIG. 4, a 1 hour equilibration step provided comparable (or better) cell viability to that of 2 hour and 4 hour equilibrations.

Example 11 Viable Chondrocytes After Cryopreservation in Various Cryopreservation Media Cartilage products made by the method detailed in Example 9 were analyzed for viable chondrocytes after cryopreservation. Various cryopreservation media were investigated to determine their effect on cell viability.

Figure 5:
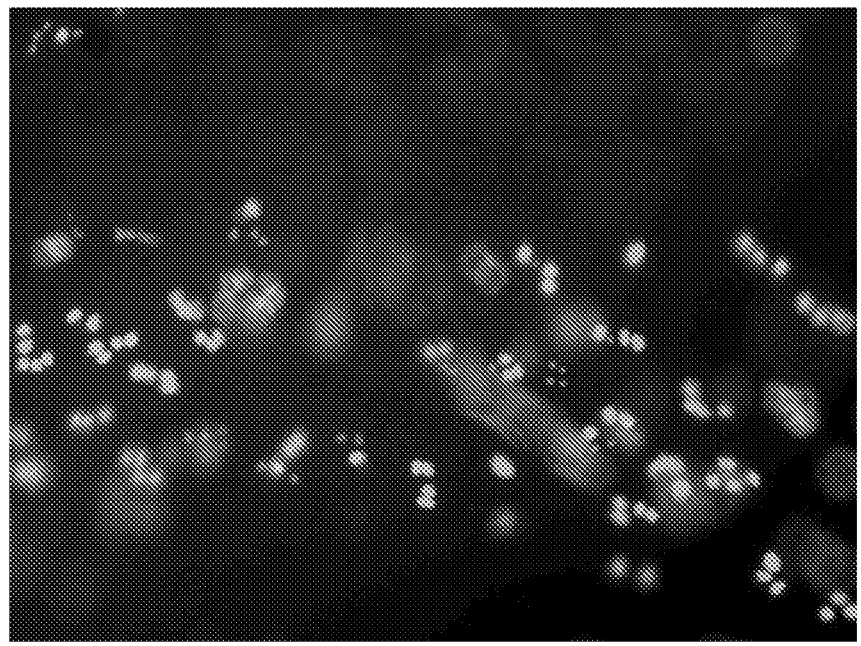
FIG. 5 depicts viable chondrocytes in cryopreserved cartilage products of the present invention.
Figure 5:
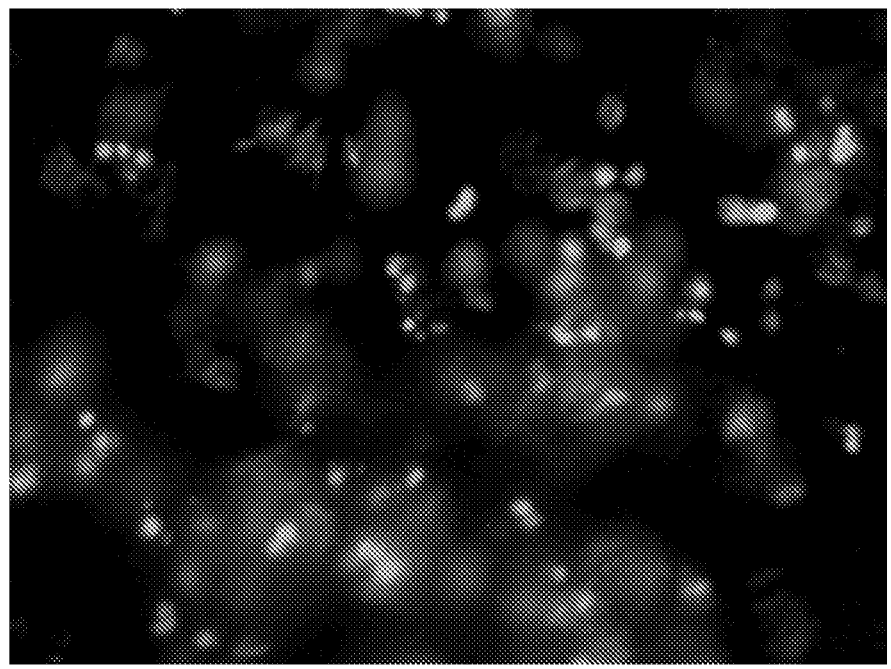

In a first experiment, cartilage products were formulated in a cryopreservation medium containing either 10% or 20% DMSO in 5% HSA in plasmalyte A. LIVE/DEAD® staining was performed on thawed cartilage products of the final cartilage product in the manner detailed in Example 10. The results are depicted in FIG. 5. There was no qualitative difference in cell viability between 10% (FIG. 5A) and 20% DMSO (FIG. 5B). Accordingly, the cartilage product can be formulated in reduced concentrations of cryopreservation medium to provide products with viable chondrocytes upon thawing.

Figure 6:
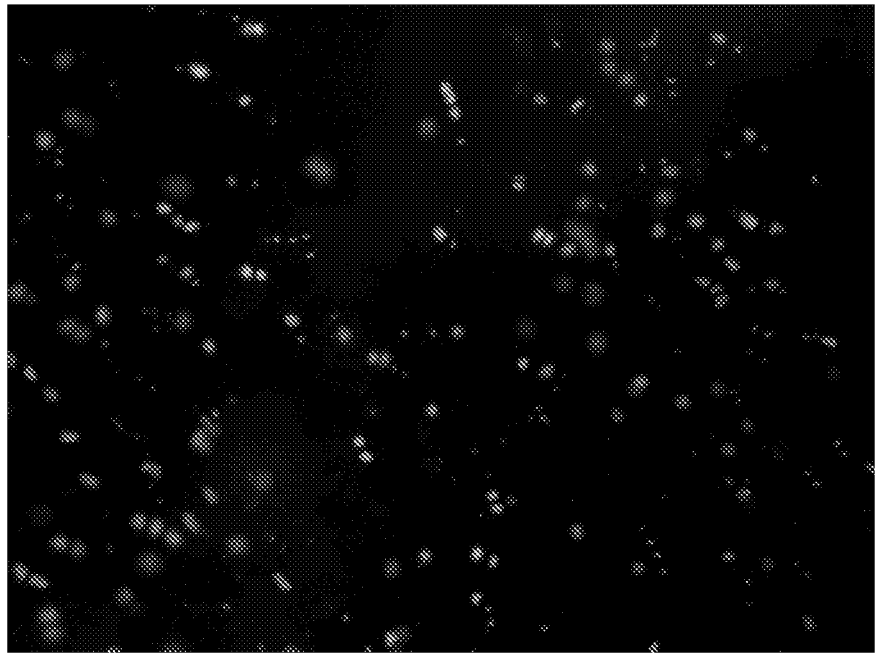
FIG. 6 depicts viable chondrocytes in cryopreserved cartilage products of the present invention.
Figure 6:
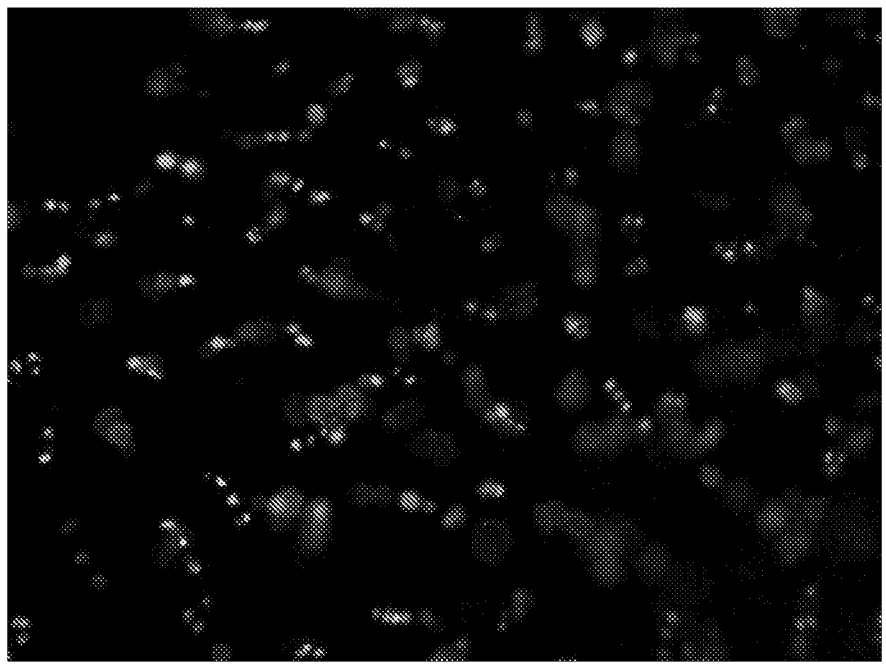

In a second experiment, cartilage products were formulated in a cryopreservation medium containing either 0% or 5% HSA and 10% DMSO in 5% HSA in plasmalyte A. LIVE/DEAD® staining was performed on thawed cartilage products of the final cartilage product in the manner detailed in Example 10. The results are depicted in FIG. 6. In this study, no remarkable difference was observed in cell viability between 0% (FIG. 6A) and 5% HSA (FIG. 6B). However, through inventor insight regarding the effect of HSA on long term stability of cryopreserved tissues, HSA is optionally included.

Figure 7:
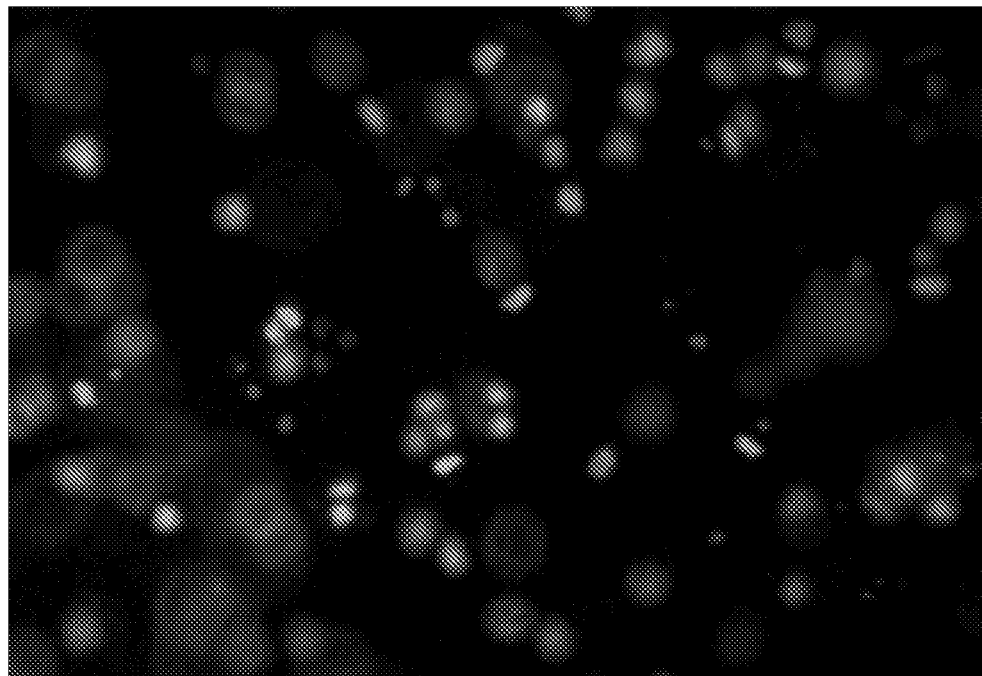
FIG. 7 depicts viable chondrocytes in cryopreserved cartilage products of the present invention.
Figure 7:
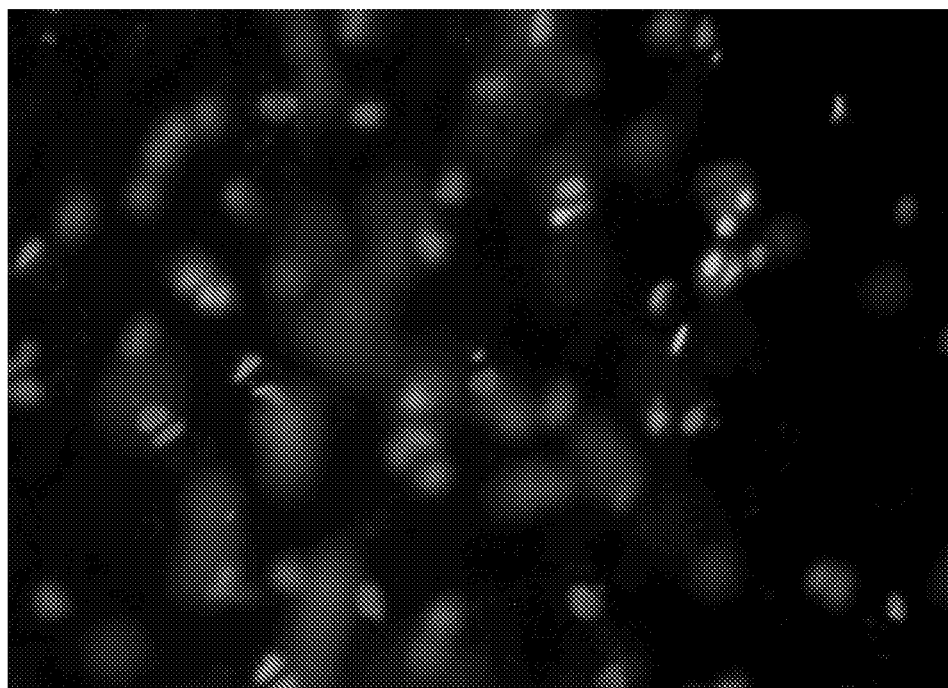

In a third experiment, cartilage products were formulated in a cryopreservation medium containing 10% DMSO+5% HSA solution in either plasmalyte-A or normal saline. LIVE/DEAD® staining was performed on thawed cartilage products of the final cartilage product in the manner detailed in Example 10. The results are depicted in FIG. 7. The results did not demonstrate a remarkable difference in cell viability between plasmalyte-A (FIG. 7A) and normal saline (FIG. 7B). However, through inventor insight, plasmalyte-A is optionally included because it contain salts and minerals (e.g. sodium chloride, sodium gluconate, sodium acetate, potassium chloride and magnesium chloride) that may be beneficial for long term stability of the cartilage product during cryogenic storage. A useful cryosolution for cartilage products of the present invention include 10% DMSO+5% HSA in plasmalyte-A.

These results indicate that the cartilage products made by the methods taught herein can contain viable chondrocytes after a freeze/thaw cycle when formulated in various cryopreservation media.

Example 12 Sustained Viability of Cells After Thawing

Cartilage products from Example 9 were analyzed for viable chondrocytes after cryopreservation. Cell viability was determined at various time points after thawing cartilage products.

Figure 8:
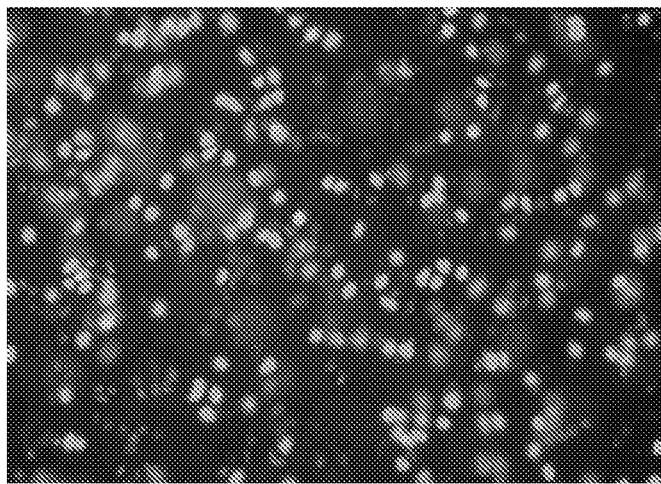
FIG. 8 depicts viable chondrocytes in cryopreserved cartilage products of the present invention.
Figure 8:
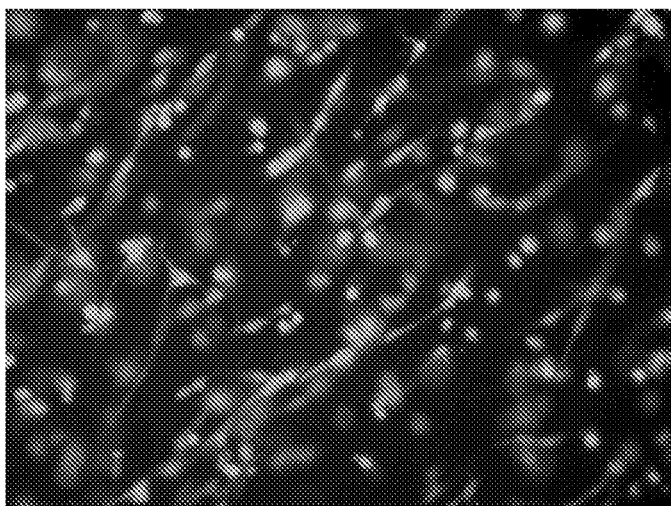
Figure 8:
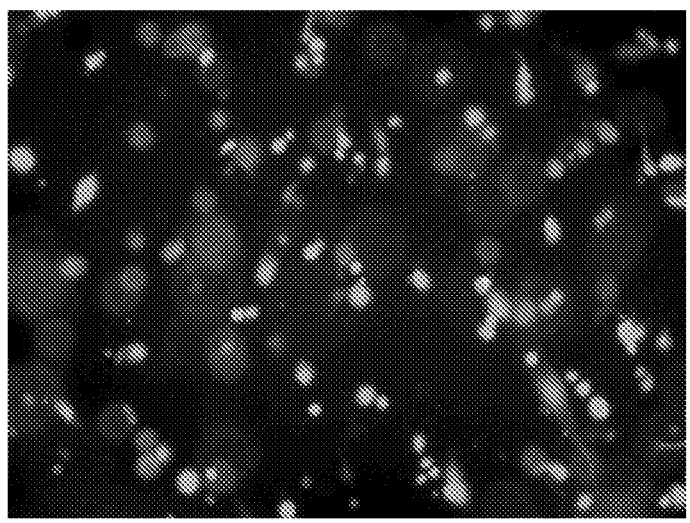

Cartilage products were formulated in a cryopreservation medium containing either 10% DMSO in 5% HSA in plasmalyte A. After cryopreservation and thawing, cartilage products were cultured in DMEM+1% HSA+antibiotic/antimycotic for up to 14 days. At 0 days (FIG. 8A), 7 days (FIG. 8B) and 14 days (FIG. 8C) of culturing, cartilage products were evaluated for LIVE/DEAD® staining in the manner detailed in Example 10. As depicted in FIG. 8, chondrocytes were viable during the 14 day culture period after a freeze/thaw cycle. Thus, cartilage products made by methods of the present invention provide a cellular component that contributes to therapeutic efficacy.

Example 13 Quantitative Evaluation of Cell Viability

Cartilage products from Example 9 were analyzed for cell number and cell viability after cryopreservation.

Cryopreserved cartilage products were thawed and thin sections were stained with LIVE/DEAD® staining as detailed in Example 10. Viable and dead chondrocytes were visualized under a 10× magnification lens and counted as indicated by either green or red fluorescence, respectively, within a 0.38 mm$^2$ field. Three random sections were analyzed from four separate donors. As detailed in Table 1, the average number of viable cells was 64,989 cells/cm$^2$ with cell viability of 70.5%. This data indicates that cartilage products made by methods of the present invention can have cells with 70% viability.

TABLE 1

| | Cell Viability | | |
|---|---|---|---|
| | Live cells/cm$^2$ | Dead cells/cm$^2$ | Viability |
| Donor 50 | | | |
| Section 1 | 46,579 | 8,421 | 85.0% |
| Section 2 | 38,947 | 10,000 | 79.6% |
| Average | 42,763 | 9,211 | 82.3% |
| Donor 53 | | | |
| Section 1 | 95,789 | 13,421 | 87.7% |
| Section 2 | 61,316 | 17,632 | 77.7% |
| Section 3 | 67,895 | 53,158 | 56.1% |
| Average | 75,000 | 28,070 | 72.8% |
| Donor 54 | | | |
| Section 1 | 57,632 | 5,789 | 90.9% |
| Section 2 | 66,316 | 11,081 | 85.7% |
| Section 3 | 76,579 | 9,211 | 89.3% |
| Average | 66,842 | 8,694 | 89.3% |
| Donor 55 | | | |
| Section 1 | 83,158 | 82,368 | 50.2% |
| Section 2 | 63,947 | 18,684 | 77.4% |
| Section 3 | 78,947 | 87,895 | 47.3% |
| Average | 75,351 | 62,982 | 54.5% |
| Total Average | 64,989 | 27,239 | 70.5% |

Example 14 Flexible Cartilage Product

In one embodiment, cartilage products made by the methods of the present invention exhibit enhanced flexibility allowing them to be administered arthroscopically. Surprisingly, by poration and optional digestion, a cartilage product can be made flexible enough to be threaded through an arthroscopic cannula; this is in contrast native articular cartilage which is normally hard with very little ability to flex without breakage.

Various pore sizes and pore densities were evaluated to determine their effect on flexibility and capacity for use in arthroscopy. Cartilage products were produced using the method detailed in Example 4 and processed further by poration alone or poration and digestions. Two different pore sizes were tested; 0.6 mm and 0.9 mm diameter pores. Three different pore densities were tested: 12, 25 and 50 pores/cm$^2$. In addition, a 30 minute collagenase digestion was also tested to evaluate the effect of digestion on the cartilage product. Various combinations of treatment conditions (treatments A-L) were evaluated, as detailed in Table 2. Each of the cartilage products produced by treatments A-L is an exemplary cartilage product of the present invention.

Specifically, each of treatment conditions A-L was labeled with a corresponding letter and 6 blinded evaluators were asked to rate the cartilage product for flexibility on a scale from 1-5 (1=most flexible and 5=hardest and least flexible). The results are depicted in Table 3. The results indicate that a larger pore size (0.9 mm diameter) and greater pore frequency (50 pores/cm$^2$) yielded the most flexible cartilage product. In this experiment, collagenase treatment did not demonstrate a remarkable difference in flexibility. However, in other experiments (data not shown), users observed much more marked change in flexibility due to collagenase treatment.

TABLE 2

Treatment Conditions

| Treatment | Description |
|---|---|
| A | 0.6 mm pores, 12 pores/cm$^2$ |
| B | 0.6 mm pores, 25 pores/cm$^2$ |
| C | 0.6 mm pores, 50 pores/cm$^2$ |
| D | 0.9 mm pores, 12 pores/cm$^2$ |
| E | 0.9 mm pores, 25 pores/cm$^2$ |
| F | 0.9 mm pores, 50 pores/cm$^2$ |
| G | 0.6 mm pores, 12 pores/cm$^2$ + collagenase treatment |
| H | 0.6 mm pores, 25 pores/cm$^2$ + collagenase treatment |
| I | 0.6 mm pores, 50 pores/cm$^2$ + collagenase treatment |
| J | 0.9 mm pores, 12 pores/cm$^2$ + collagenase treatment |
| K | 0.9 mm pores, 25 pores/cm$^2$ + collagenase treatment |
| L | 0.9 mm pores, 50 pores/cm$^2$ + collagenase treatment |

TABLE 3

Flexibility of Cartilage Products After Various Treatment Conditions

| Condition | Eval # 1 | Eval # 2 | Eval # 3 | Eval # 4 | Eval #5 | Eval #6 | Average |
|---|---|---|---|---|---|---|---|
| A | 5 | 5 | 4 | 5 | 5 | 5 | 4.8 |
| B | 5 | 4 | 4 | 5 | 5 | 5 | 4.7 |
| C | 4 | 4 | 4 | 3 | 3 | 3 | 3.5 |
| D | 5 | 4 | 3 | 4 | 4 | 2 | 3.7 |
| E | 4 | 4 | 3 | 3 | 3 | 1 | 3.0 |
| F | 3 | 3 | 2 | 2 | 2 | 1 | 2.2 |
| G | 5 | 5 | 5 | 5 | 5 | 5 | 5.0 |
| H | 5 | 5 | 5 | 5 | 5 | 5 | 5.0 |
| I | 4 | 4 | 5 | 4 | 4 | 3 | 4.0 |
| J | 5 | 4 | 4 | 4 | 3 | 2 | 3.7 |
| K | 4 | 4 | 3 | 3 | 4 | 1 | 3.2 |
| L | 3 | 3 | 2 | 2 | 2 | 1 | 2.2 |

Example 15 Non-Immunogenicity of Cartilage Products

Cartilage products made by the method detailed in Example 9 were analyzed for immunogenicity. Specifically, secretion of TNF-α by cartilage products in response to lipopolysaccharide (LPS) was used to determine immunogenicity. The secretion of TNF-α of cryopreserved cartilage products of the present invention was compared to that of raw (fresh) cartilage products.

Pieces (0.785 cm$^2$) of cartilage products (raw vs. cryopreserved) were placed in tissue culture medium and exposed to bacterial LPS (1 µg/mL, Sigma) for 20-24 hr. After 24 hours, tissue culture media were collected and tested for the presence of TNF-α using a TNF-α ELISA kit (R&D Systems) according to manufacturer's protocol. Human hPBMCs, known to contain monocytes that secrete high levels of TNF-α upon LPS stimulation, were used as a positive control in the assay. hPBMCs and cartilage products without LPS were also included as controls in the analysis.

Figure 9:
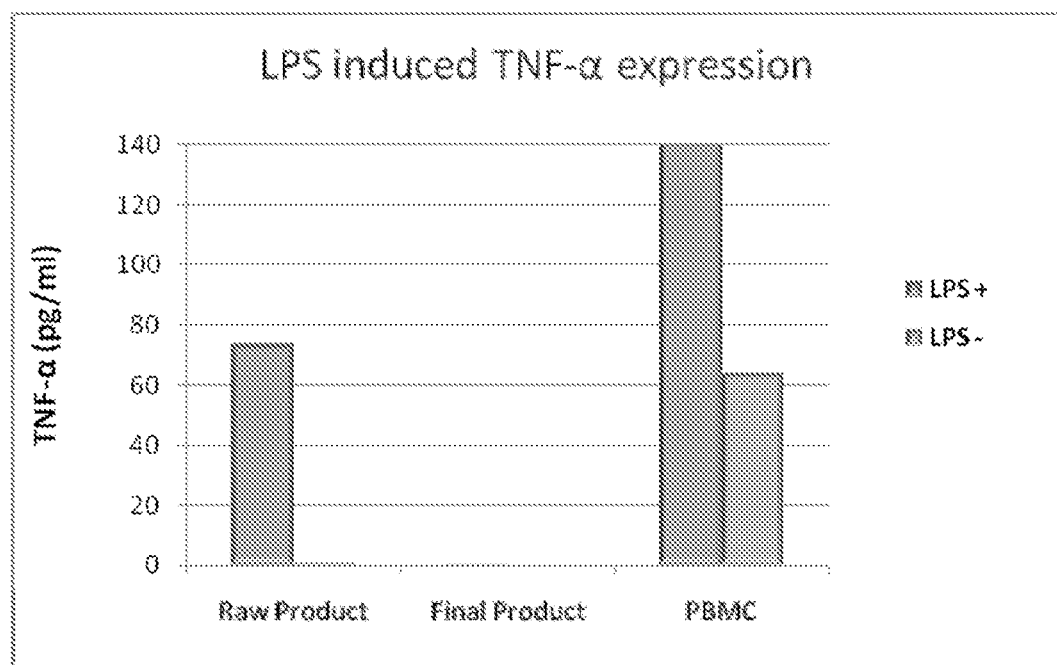
FIG. 9 depicts non-immunogenicity of cartilage products of the present invention.

The results are depicted in FIG. 9. Non-cryopreserved cartilage products ("raw product") provided substantial levels of TNF-α in response to LPS while cryopreserved cartilage products ("final product") did not provide substantial levels of TNF-α in response to LPS, indicating that the manufacturing process eliminates immunogenicity of cartilage samples. Without being bound by theory, the inventors believe that viable functional macrophages are the source of immunogenicity in the unprocessed cartilage.

Surprisingly, these results indicate that cartilage products made by methods of the present invention can be selectively depleted of macrophages to reduce immunogenicity of allogeneic implants.

Example 16 Bioactive Factors in Cartilage Products

Cartilage products made by the method detailed in Example 9 were analyzed for the presence of bioactive factors. Specifically, Enzyme-Linked Immunosorbent Assays (ELISAs) were used to analyze tissue extracts and factors released in cultured supernatants of the cartilage products.

For the tissue extract assay, cryopreserved cartilage products of Example 9 were thawed in a 37° C. water bath and removed from the cryopreservation medium followed by a PBS rinse. Each product was then finely minced and snap frozen in a homogenization tube in a liquid nitrogen bath. One pre-cooled 5 mm steel bead was added to each tube and homogenized using a Qiagen Tissue Lyser according to the manufacture's recommendations in 1 ml homogenization media. Homogenates were then spun down at 16000 g for 10 minutes using a microcentrifuge. Supernatants were collected and stored at −80° C. until analyzed by ELISA for protein expression. The supernatant volume was approximately equal to that of the initial volume of homogenization media (1 ml).

For the factor release assay, cryopreserved cartilage products were thawed in a 37° C. water bath and removed from the cryopreservation medium followed by a PBS rinse. Each cartilage product was plated onto a well of a 12-well dish and 2 ml of growth media (DMEM+1% HSA+antibiotic/antimycotic) was added and incubated at 37° C. for up to 14 days. After incubation, tissue and culture media were transferred to a 15 ml conical tube and centrifuged at 2000 rpm for 5 min. Culture supernatant was collected analyzed by ELISA for protein expression. The supernatant volume was approximately equal to that of the initial volume of growth media (2 ml).

Table 4 lists examples of chondrogenic factors detected in the tissue extract and factor release assays. Each expression value is provided in terms of amount of factor per supernatant volume per superior surface area (identified in FIG. 15)

of the cartilage product (pg/ml/cm$^2$) and amount of factor per superior surface area of the cartilage product (pg/cm$^2$).

TABLE 4

Chondrogenic Factors

| Factor | Range of expression in tissue lysates (pg/cm$^2$) | Range of factors released in culture supernatants (adjusted per cm$^2$ of tissue) (pg/ml) |
|---|---|---|
| TGF-β1 | 10.8-627.8 | 2616.6-17818 |
| TGF-β2 | TBD | 133-623 |
| TGF-β3 | 3.98-112.1 | TBD |
| BMP-2 | TBD | TBD |
| BMP-7 | 3.33-23.3 | TBD |
| bFGF | 168.8-365 | TBD |
| IGF-1 | 111-779 | 14-2842 |
| ECM (Collagen type II, Hyaluronan, Aggrecan) | TBD | TBD |

Without being bound by theory, the inventors believe that bioactive factors (e.g. growth factor proteins) that mediate extracellular matrix production and promote chondrogenesis are important to efficient cartilage repair as facilitated by the cartilage products of the present technology.

Surprisingly, these results indicate that the cartilage products made by the methods of the present invention comprises a variety of chondrogenic factors that facilitate therapeutic value in articular cartilage repair.

Example 17 Sustained Release of Proteins from Cartilage Products

Cartilage products made by methods of the present invention can release factors into the microenvironment by cells or tissues to enhance their functional activity.

Figure 10:
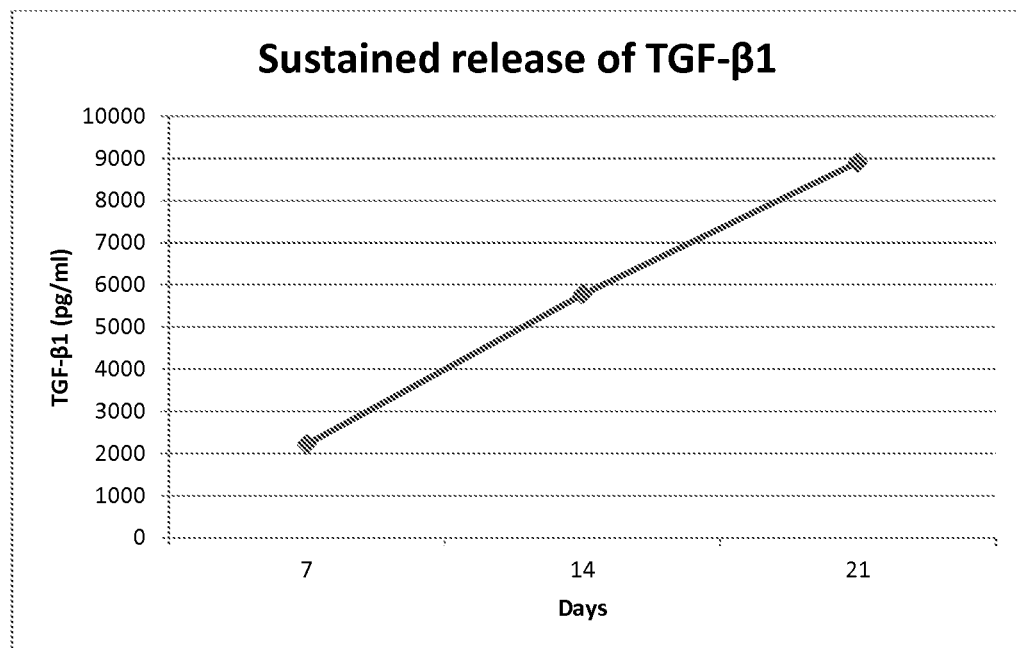
FIG. 10 depicts sustained release of chondrogenic factors from cartilage products of the present invention.
Figure 10:
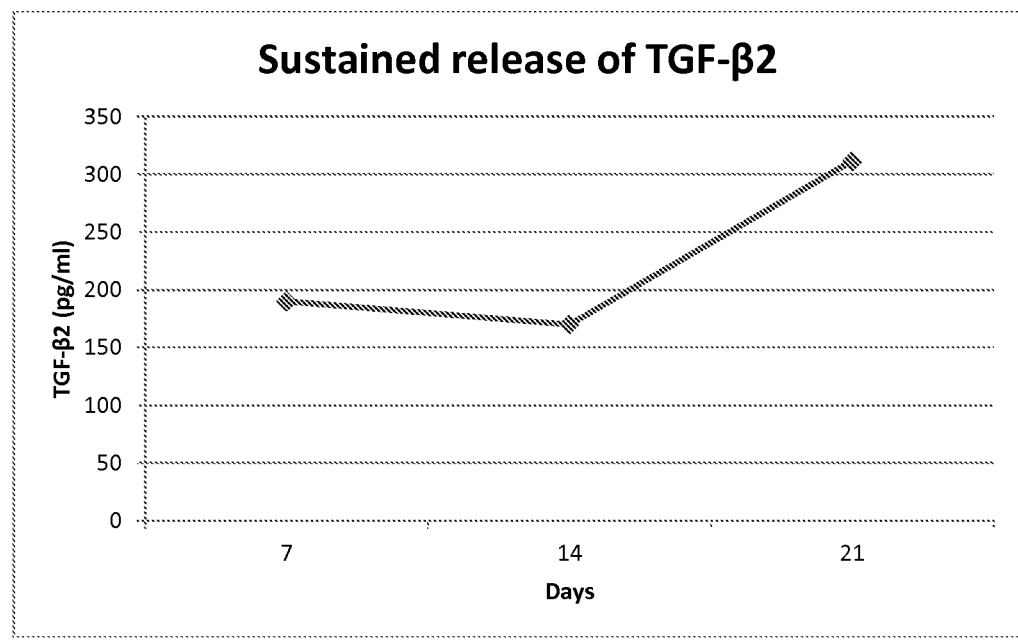

To measure the amount or proteins released, cartilage products of Example 9 were cultured in culture media between 7-21 days and supernatants were collected and key proteins were quantified by ELISA. The results are depicted in FIG. 10, which indicate that the cartilage products produce and release TGF-β1 and TGF-bβ into the supernatant for at least 21 days. These data indicate that the cartilage product has the ability to produce and sustain chondrogenic growth factors levels over time due to the presence of viable chondrocytes and dense ECM.

Example 18 Factor Release From Porated Cartilage Products

Figure 11:
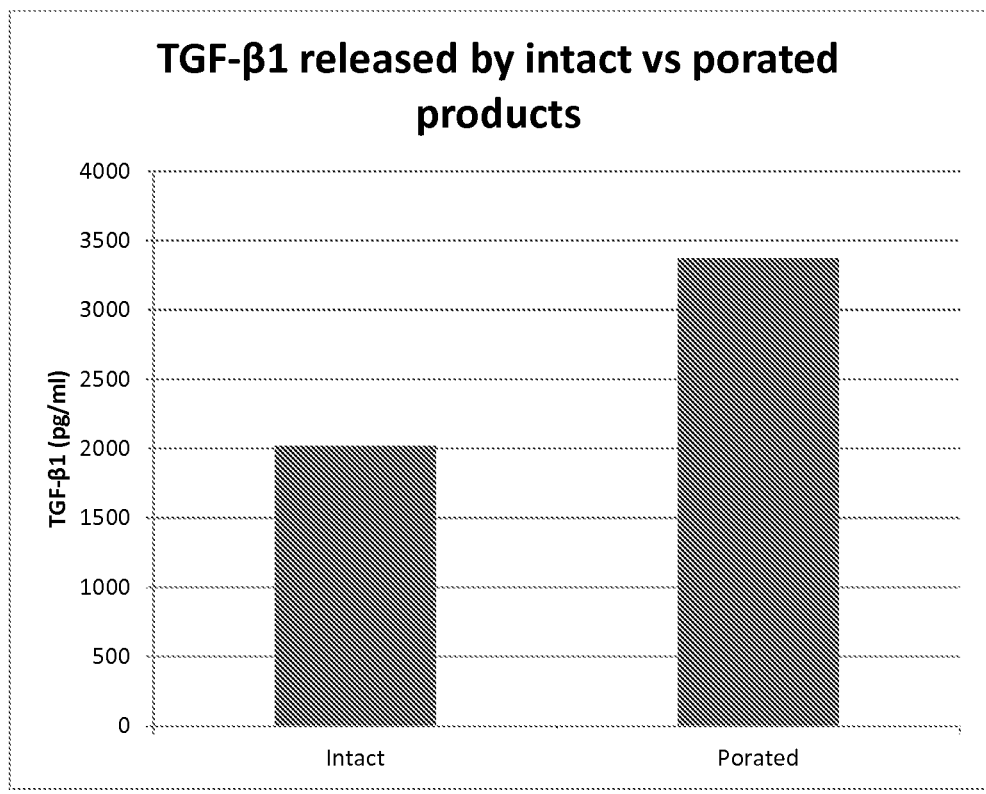
FIG. 11 depicts greater release of chondrogenic factors from porated cartilage products of the present invention.

The effect of poration versus intact cartilage products on protein was investigated. Cartilage products were generated as detailed in Example 9 except that the poration parameters were modified. Half the products were porated between 36-50 pores/cm$^2$ while the rest were kept intact with no poration. The amount of TGF-I31 was measured by ELISA from supernatants of both conditions of cartilage products cultured for 7 days. The results are depicted in FIG. 11, which indicate that the amount of TGF-β1 released from porated cartilage implants is greater than intact cartilage products. These data indicate that not only do the porations within the product contribute to the flexibility of the product but poration also supports greater release of chondrogenic factors. Without being bound by theory, the inventors speculate that the enhanced release is due to the increased surface area created by the pores.

Example 19 Factor Release from Digested Cartilage Products

Figure 12:
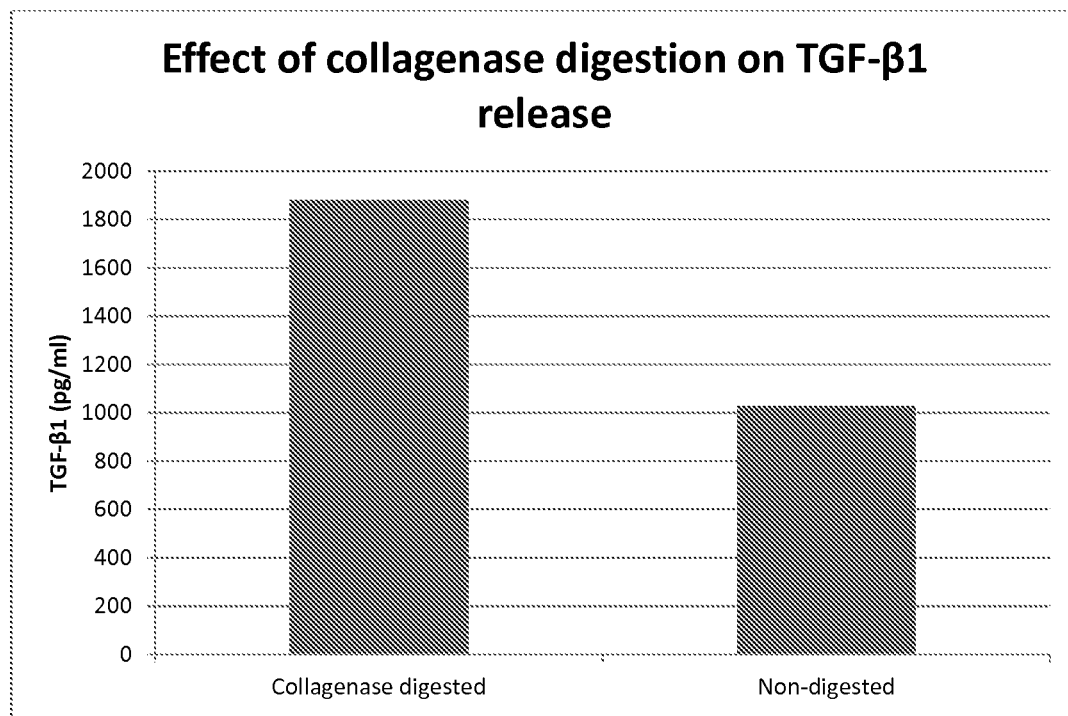
FIG. 12 depicts greater release of chondrogenic factors from digested cartilage products of the present invention.

The effect of digestion of cartilage products on protein release was investigated. Cartilage products were generated as detailed in Example 9 except that the digestion parameters were modified. Half the products did not undergo the 30 minute collagenase digestion prior to cryopreservation. The amount of TGF-β1 released was measured by ELISA from supernatants of both conditions of products cultured for 14 days. The results are depicted in FIG. 12 which demonstrates that the amount of TGF-β1 released from collagenase digested cartilage products is greater than non-digested cartilage products. These data indicate that not only does collagenase digestion contribute to the flexibility and cleanliness of the product but digestion also supports greater release of beneficial proteins to the microenvironment.

Example 20 TGF-β Factor Release from Cryopreserved Cartilage Products Containing Live Cells The effect of cryopreservation on protein release was investigated. Cartilage products were generated as detailed in Example 9 (i.e. cryopreserved). Next, some cartilage products underwent an additional three freeze thaws in H$_2$O to kill all the cells within the product ("devitalization"). As a final step, all cartilage products were thawed and cultured in separate wells in growth media for 21 days.

Figure 13:
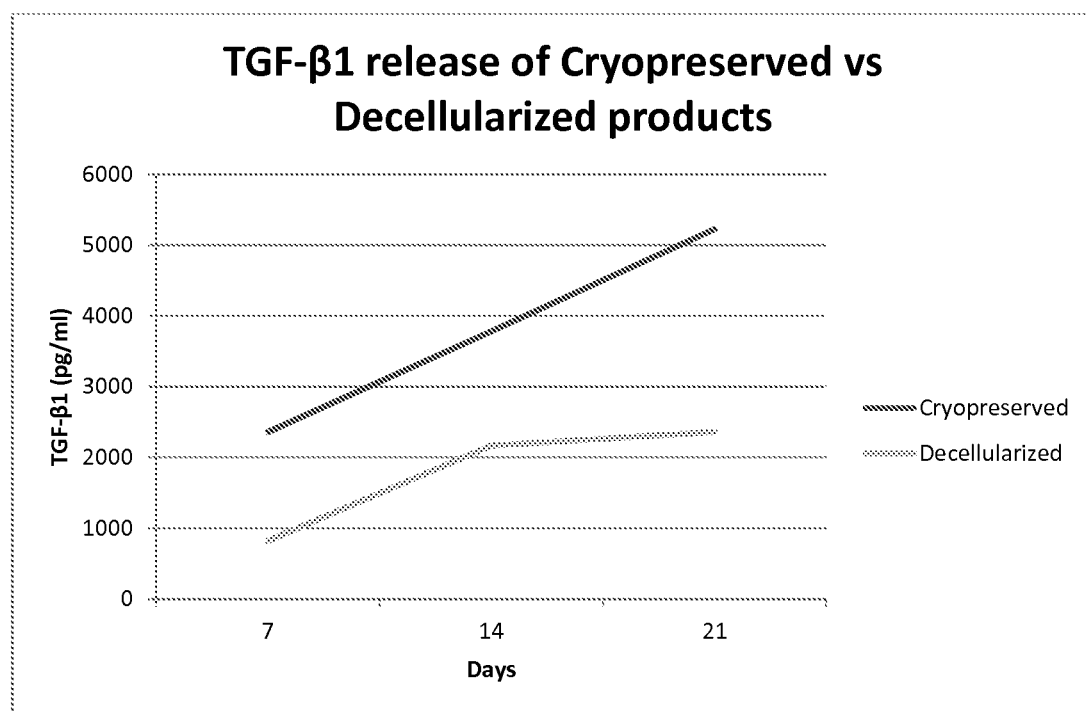
FIG. 13 depicts greater release of chondrogenic factors from cryopreserved cartilage products of the present invention.

The amount of TGF-β1 spontaneously released into the media was measured by ELISA from supernatants of both conditions of cartilage products cultured for the 21 days. The results are depicted in FIG. 13, which demonstrates that the amount of factor (TGF-β1) released from cryopreserved cartilage products containing live cells is greater than devitalized cartilage products all throughout the 21 day culture. These data indicate that cryopreserved cartilage products contain viable cells that continue to produce and contribute beneficial factors such as TGF-β1 to the microenvironment as compared to cartilage without living cells.

Example 21 Cell Viability After Povidone-Iodine Treatment of Cartilage Products

Efforts to optimize the aseptic processing of donor tissue are important for therapeutic use (and, e.g., in order to comply with the Food & Drug Administration (FDA) and tissue bank regulations regarding tissue product safety). To minimize incoming bioburden carried by the donor tissue, cartilage products were treated with an overnight antibiotic incubation prior to cryopreservation, as detailed in Example 7. To further decrease bioburden of the cartilage product, povidone-iodine treatment was tested to observe any changes in cell viability or protein expression. Povidone-iodine is a potent antiseptic widely used to in the clinic to cleanse and decontaminate surgical surfaces.

Briefly, cartilage products were produced as detailed in Example 9, however, prior to overnight antibiotic incubation, cartilage products were submerged in a povidone-iodine bath for 1 sec and then immediately washed in saline 3 times. Cartilage products then followed the normal antibiotic incubation and cryopreservation process. To assess the effect of povidone-iodine treatment, cell viability (LIVE/

Figure 14:
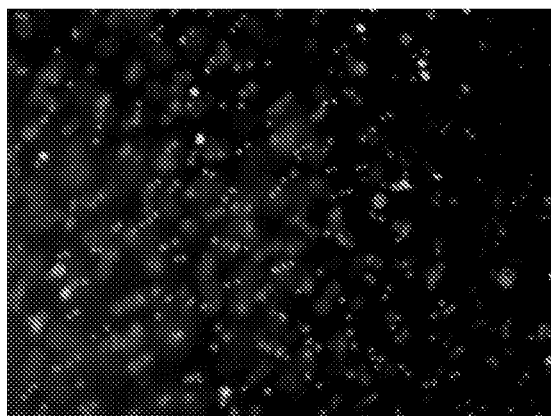
FIG. 14 depicts the effect of iodine treatment on cell viability.
Figure 14:
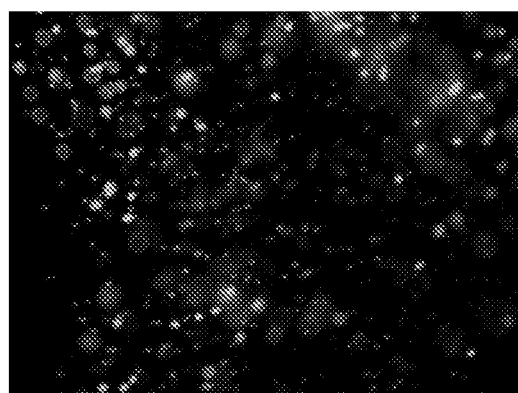
Figure 14:
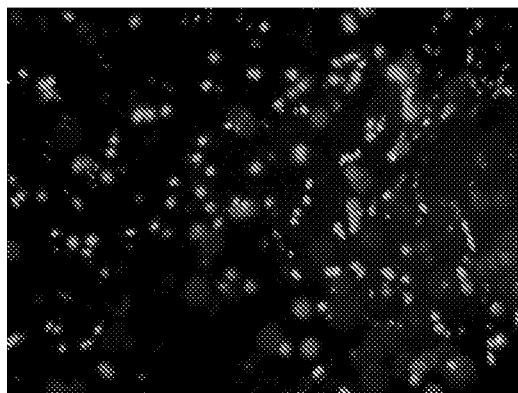
Figure 14:
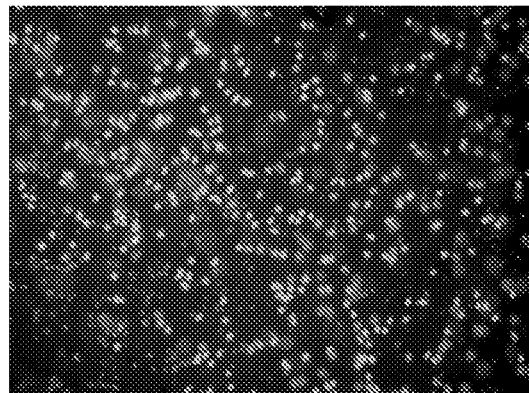

DEAD® staining) was analyzed as detailed in Example 10. The results are depicted in FIG. 14. Three concentrations of povidone-iodine were tested, 10% povidone-iodine (FIG. 14A), 5% povidone-iodine (FIG. 14B), 1% povidone-iodine (FIG. 14C), and 0% povidone iodine as a control (FIG. 14D). The LIVE/DEAD® staining of thawed cartilage products revealed that with increasing concentrations of povidone-iodine, cell viability also decreased compared to the control untreated cartilage product.

Example 22 Treatment of Chondral Defects in Goats with Cartilage Products

In one embodiment, the efficacy of a cartilage product produced by methods taught herein are tested in an animal model, e.g. an animal model of focal chondral defects.

Briefly, focal chondral defects are induced into stifle joints of a goat and then treated with microfracture alone or microfracture with cartilage products (as produced in Example 9). At 3, 6 and 12 months, joints are collected and repair tissue is analyzed for volume of defect filling as well as collagen type II staining indicating formation of articular cartilage repair tissue. In addition, goats can be evaluated for safety of the product by monitoring for inflammation or general discomfort of the animal throughout the duration of the study.

Cartilage products of the present technology substantially increase cartilage repair according to at least one or more of the following non-limiting criteria.
  Safety
  Gross morphology
  Quality of repair tissue relative to native surrounding tissue
  Integration of repair tissue
  Histological evaluation
  Extracellular matrix staining
  Defect volume filling
  Mechanical evaluation
  Indentation testing of repair tissue
  Repair tissue evaluation via O'Driscoll grading system Example 23 Chondrogenesis of Viable Cells within Cartilage Products This study demonstrates that the viable cells within the cartilage product made by the present methods are functional and have the potential to lay down healthy ECM that will contribute to proper cartilage repair.

Chondrocytes are isolated and expanded from cartilage products of the present invention. Prolonged in vitro culturing of chondrocytes results in dedifferentiation of some cells (e.g. to a more primitive fibroblastic lineage). Next, these cells are placed in a differentiation medium (e.g. containing growth factors). Over time, these cells demonstrate chondrogenesis in vitro.

Example 24 Gene Expression of Chondrocytes within Cartilage Products

Cartilage products are generated as detailed in Example 9 (except, with and without cryopreservation). Chondrocytes within the cartilage product are examined for the expression of essential genes that stimulate functionally active chondrocytes. Substantial expression levels of the following are detected: collagen type II, aggrecan, SOX5, SOX6, and SOX9.

Example 25

The Stimulatory Effect of Chondrocytes in Cartilage Products on Exogenous MSCs

Isolated mesenchymal stem cells (e.g. from a different donor) are co-cultured with chondrocytes isolated from cartilage products made by methods of the present invention.

The chondrocytes stimulate MSCs to differentiate to chondrocytes and stimulate the resultant chondrogenesis in this model. These results demonstrate that therapeutic efficacy of cartilage products of the present invention is due, in part, to the stimulatory effect of chondrocytes of the cartilage product on recipient MSC cells.

The citations provided herein are hereby incorporated by reference for the cited subject matter.

Further embodiments of the present invention can be found in the following paragraphs.

In some embodiments, the present technology provides a method of producing a cartilage product comprising: (a) providing a cartilage sample; (b) porating the cartilage sample; and (c) partially digesting the cartilage sample. In some embodiments, the method includes providing a cartilage sample, wherein the cartilage sample comprises type II collagen, optionally wherein the sample comprises hyaline cartilage. In some embodiments, the cartilage sample has a thickness of about 0.3 mm to about 2.0 mm, optionally wherein said thickness is about 1.0 mm to about 1.5 mm. In another embodiment, the hyaline cartilage is selected from: articular cartilage, condoyle cartilage, femur condoyle cartilage, and tibial plateau cartilage.

In some embodiments, the method includes providing a cartilage sample that is devoid of subchondral bone, optionally wherein the cartilage product is devoid of a calcified cartilage layer. In other embodiments, the method includes providing the cartilage sample comprising isolating the cartilage sample from subchondral bone.

In another embodiment, the method includes providing the cartilage sample, wherein the cartilage sample comprises: (a) isolating a sample comprising articular cartilage and subchondral bone; and (b) removing the subchondral bone from the articular cartilage; and (c) optionally, removing calcified cartilage from the articular cartilage. In some embodiments, the method of the present technology includes providing a cartilage sample, wherein the cartilage sample comprises a radial layer, a transitional layer, and a tangential layer.

In some embodiments, the method of the present technology provides poration that provides pores extending through: (a) the radial layer; (b) the transitional layer; (c) the tangential layer; (d) a and b; or (e) a, b, and c. In some embodiments, the poration provides pores that are substantially perpendicular to said layers.

In yet another embodiment, the present technology provides a method wherein the cartilage sample comprises a layer of cartilage selected from: a radial layer, a transitional layer, and a tangential layer. In some embodiments, the poration provides pores that are substantially perpendicular to said layer.

In some embodiments, the present technology provides a method of producing a cartilage product wherein the cartilage sample has a thickness of less than about 3 mm. In another embodiment, the cartilage sample has a thickness of about 0.5 mm to about 2 mm or about 1 mm to about 1.5 mm.

In some embodiments, the present technology provides a method of producing a cartilage product wherein porating the cartilage sample at about 10 to about 100 or about 20 to about 60 pores per cm$^2$.

In another embodiment, the method of the present technology provides a method of producing a cartilage product wherein porating the cartilage sample comprises providing a plurality of pores having a diameter selected from: about 0.3 mm to about 2 mm, about 0.5 mm to about 1.5 mm, about 0.8 mm to about 1.2 mm, or about 1 mm. In some embodiments, the pores pass through the majority of the thickness of the cartilage sample thickness. In yet other embodiments, the pores pass through the entire thickness of the cartilage sample.

In some embodiments, the method includes porating comprise mechanically removing cartilage from the cartilage sample.

In another embodiment, the step of partially digesting the cartilage sample comprises digesting the cartilage to an extent that retains viable native cells, optionally, wherein the viable native cells are chondrocytes. In some embodiments, the extent is an amount of digestion that results in retaining of a substantial amount of viable chondrocytes per cm$^2$, optionally wherein the substantial amount is a majority of the viable chondrocytes per cm$^2$ relative to an undigested cartilage sample.

In some embodiments, the step of partially digesting the cartilage comprise enzymatic digestion. In some embodiments, the enzyme is a proteinase. In some embodiments, the proteinase is a collagenase, optionally wherein the collagenase is a collagenase II.

The method of the present technology may further comprise treating the cartilage sample with an antibiotic.

In some embodiments, the method of the present technology further comprises cryopreserving the cartilage sample, optionally wherein said cryopreserving is performed after said porating and partial digestion. In some embodiments, the method further comprising thawing the cryopreserved cartilage sample.

In some embodiments, the method of the present technology further comprises periodically chilling the cartilage sample during said step of porating, partial digesting, or a combination thereof Some embodiments include a cartilage product produced by the method of the present technology.

Another embodiment includes a method of treatment comprising administering to a subject in need thereof, a cartilage product produced by the methods of the present technology. In some embodiments, the cartilage product is administered arthroscopically. In some embodiments, administering comprises folding or rolling the cartilage product. In some embodiments, the step of administering is performed in conjunction with a microfracture procedure.

Some embodiments of the method of the present technology further comprising cryopreserving the cartilage sample, optionally wherein said cryopreserving is performed after said porating and partial digestion. In some embodiments, the cryopreservation comprises incubating for a period of time the cartilage sample at one or more temperatures intermediate of room temperature and −80° C. In some embodiments, said one or more temperatures intermediate of room temperature and −80° C. comprises at least two independent temperatures. In some embodiments, the period of time is at least about 10 min, at least about 20 min, or at least about 30 min, optionally wherein said period of time less than about 24 hours.

In some embodiments, the present method comprises cryopreservation, wherein the cryopreservation comprises: (a) incubating the cartilage product for a first period of time at about 0° C. to about 10° C.; (b) incubating the cartilage product for a second period of time at about 0° C. to about 10° C.; or (c) both a) and b). In some embodiments, the first period of time is greater than about 10 minutes, optionally wherein the first period of time is less than about 24 hours or less than about 1.5 hours. In some embodiments, the second period of time is greater than about 10 minutes, optionally wherein the first period of time is less than about 12 hours or less than about 1 hour.

In some embodiments, the cartilage sample has a surface area of about 0.8 cm$^2$ to about 13 cm$^2$.

In some embodiments, the cartilage sample is a primate cartilage sample or a human cartilage sample, optionally having a surface area of about 0.8 cm$^2$ to about 13 cm$^2$.

In some embodiments, the method of the present technology wherein the cartilage product further comprises an additive.

What is claimed is:

1. A flexible cryopreserved partially digested cartilage material comprising non-cultured cartilage isolated from a subject, wherein:
    the material comprises an extracellular matrix, growth factors, and chondrocytes,
        wherein the extracellular matrix, growth factors, and chondrocytes were embedded in the material when it was isolated from the subject, and
        wherein at least 70% of the chondrocytes are viable; and
    the material has a first circular-shaped surface, an opposing second circular-shaped surface, and a thickness of 0.2 millimeters (mm) to 2 mm,
        wherein the first circular-shaped surface has an array of cavities capable of facilitating migration of the chondrocytes,
    wherein, after cryopreserving, the material retains the structural and functional properties of natural cartilage,
    wherein digestion of the material is limited to an amount that preserves the viability of the chondrocytes and/or the structural and functional properties of natural cartilage, and
    wherein digestion is performed in a manner that retains interaction between the extracellular matrix and the chondrocytes.

2. The flexible cryopreserved cartilage material of claim 1, wherein the growth factors comprise basic fibroblast growth factor (bFGF) and transforming growth factor beta 1 (TGF-β1).

3. The flexible cryopreserved cartilage material of claim 2, wherein the growth factors further comprise bone morphogenic protein 2 (BMP-2).

4. The flexible cryopreserved cartilage material of claim 3, wherein the growth factors further comprise insulin-like growth factor 1 (IGF-1) and bone morphogenic protein 7 (BMP-7).

5. The flexible cryopreserved cartilage material of claim 1, wherein the extracellular matrix comprises collagen fibrils that include type II collagen.

6. The flexible cryopreserved cartilage material of claim 1, wherein the cartilage is hyaline cartilage.

7. The flexible cryopreserved cartilage material of claim 1, wherein the array of cavities is arranged in a grid pattern.

8. The flexible cryopreserved cartilage material of claim 1, wherein the second circular-shaped surface does not have an array of cavities capable of facilitating migration of the viable chondrocytes.

9. The flexible cryopreserved cartilage material of claim 1, wherein the material is flexible such that it capable of being, rolled, folded, or bent without breaking.

10. The flexible cryopreserved cartilage material of claim 1, wherein the cartilage material comprises a radial layer, a transitional layer, and a tangential layer.

11. The flexible cryopreserved cartilage material of claim 1, wherein the material is disk-shaped.

12. The flexible cryopreserved cartilage material of claim 11, wherein the material has a diameter of 10 millimeters (mm) to 20 millimeters (mm).

13. The flexible cryopreserved cartilage material of claim 11, wherein the material has a diameter of 20 millimeters (mm).

14. The flexible cryopreserved cartilage material of claim 1, wherein the material is comprised within a cryopreservation medium.

15. The flexible cryopreserved cartilage material of claim 1, wherein at least 80% of the chondrocytes are viable.

16. The flexible cryopreserved cartilage material of claim 1, wherein the flexible cryopreserved cartilage material is stored at a temperature of 0° C. to 10° C.

17. The flexible cryopreserved cartilage material of claim 1, wherein the flexible cryopreserved cartilage material is stored at a temperature of −75° C. to −85° C.

18. A method of administering a flexible cryopreserved cartilage material of claim 1 to a person, the method comprising administering the cartilage material to the person.

19. The method of claim 18, wherein the cartilage material is thawed prior to administering the cartilage material to the person.

20. The method of claim 19, wherein the thawed cartilage material has a temperature of about 37° C.

21. The method of claim 18, wherein the cartilage material is administered arthroscopically to the person.

22. The method of claim 18, wherein injured cartilage is removed from the person and replaced with the cartilage material.

23. The method of claim 22, wherein the injured cartilage is articular cartilage.

24. The method of claim 22, wherein the removed injured cartilage is disc-shaped, and wherein the cartilage material is disc-shaped.

25. The method of claim 18, wherein the cartilage material promotes chondrogenesis in the person.

26. The method of claim 18, wherein the array of cavities on the first circular-shaped surface is arranged in a grid pattern.

* * * * *